United States Patent [19]

Nelson

[11] 4,175,202
[45] Nov. 20, 1979

[54] 4,5,6-TRINOR-3,7,-INTER-M-PHENYLENE PROSTAGLANDIN A₁ ANALOGS

[75] Inventor: Norman A. Nelson, Galesburg, Mich.

[73] Assignee: The Upjohn Company, Kalamazoo, Mich.

[21] Appl. No.: 920,571

[22] Filed: Jun. 29, 1978

Related U.S. Application Data

[60] Division of Ser. No. 764,359, Jan. 31, 1977, Pat. No. 4,118,577, which is a continuation-in-part of Ser. No. 677,874, Apr. 19, 1976, abandoned, which is a division of Ser. No. 604,158, Aug. 13, 1975, abandoned.

[51] Int. Cl.² ............................................. C07C 177/00
[52] U.S. Cl. ........................................ 560/53; 562/463
[58] Field of Search ............................. 560/53; 562/463

[56] References Cited
PUBLICATIONS
Derwent Abstr. 48794y/28, BE850-204, 07/07/77.

*Primary Examiner*—Paul J. Killos
*Attorney, Agent, or Firm*—Morris L. Nielsen

[57] ABSTRACT

This invention is a group of 4,5,6-trinor-3,7-inter-m-phenylene prostaglandin-type compounds and processes for making them. These compounds are useful for a variety of pharmacological purposes, including hypotensive control and inhibition of platelet aggregation.

A typical formula for a PGA₁ type analog is:

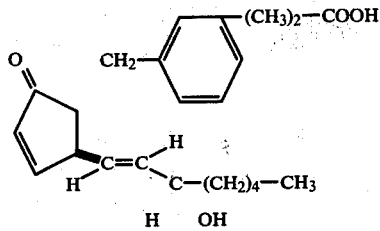

62 Claims, No Drawings

4,5,6-TRINOR-3,7,-INTER-M-PHENYLENE PROSTAGLANDIN A₁ ANALOGS

CROSS REFERENCE TO RELATED APPLICATIONS

This is a division of application Ser. No. 764,359, filed Jan., 31, 1977 now U.S. Pat. No. 4,118,577 which is in turn a continuation-in-part of application Ser. No. 677,874 filed Apr. 19, 1976 now abandoned which was a divisional of then co-pending application Ser. No. 604,158 filed Aug. 13, 1975 and since abandoned.

BACKGROUND OF THE INVENTION

This invention relates to compositions of matter, and to methods and intermediates for producing them. In particular, the several aspects of this invention relate to novel phenylene analogs of some of the known prostaglandins, i.e. prostaglandin $E_1$ ($PGE_1$), prostaglandin $F_{1\alpha}$ ($PGF_{1\alpha}$), and prostaglandin $A_1$ ($PGA_1$).

Each of the above-mentioned known prostaglandins is a derivative of prostanoic acid which has the following structure and atom numbering:

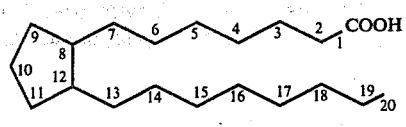

I

A systematic name for prostanoic acid is 7-[(2β-octyl)-cyclopent-1α-yl]heptanoic acid.

$PGE_1$ has the following structure:

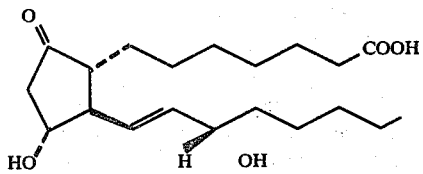

II $PGF_{1\alpha}$ has the following structure:

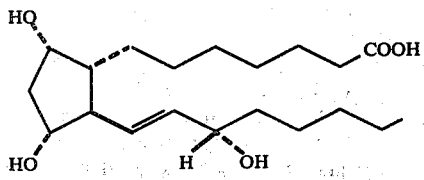

III $PGA_1$ has the following structure:

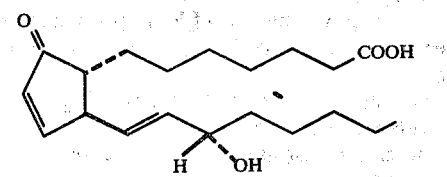

IV

The prostaglandin formulas mentioned above each have several centers of asymmetry. As drawn, formulas II–IV each represents the particular optically active form of the prostaglandin obtained from certain mammalian tissues, for example, sheep vesicular glands, swine lung, and human seminal plasma, or by reduction or dehydration of a prostaglandin so obtained; see, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1866) for discussion of the stereochemistry of the prostaglandins.

In the formulas II–IV above, as well as in the formulas given hereinafter, broken line attachments to the cyclopentane ring indicate substituents in alpha configuration, i.e., below the plane of the cyclopentane ring. See, for example, C-8 and C-11 in the $PGE_1$ formula above. Likewise, the side-chain hydroxy at C-15 in the formulas above is in alpha (S) configuration. See R. S. Cahn, Journal of Chemical Education 41, 116 (1964) for a discussion of S and R configurations. Heavy solid line attachments to the cyclopentane ring indicate substituents in beta configuration, i.e., above the plane of the cyclopentane ring.

$PGE_1$, $PGF_{1\alpha}$, and $PGA_1$ and their esters, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic blood pressure lowering in anesthetized pentolinium-treated rats with indwelling aortic and right heart cannulas; stimulation of smooth muscle as shown, for example, by tests on strips of guinea pigileum, rabbit duodenum, or gerbil colon; decrease of blood platelet adhesiveness, and inhibition of blood platelet aggregation.

Because of these biological responses, these known prostaglandins are useful to study, prevent, control, or alleviate a wide variety of diseases and undesirable physiological conditions in birds and mammals, including humans, useful domestic animals, for example, mice, rats, rabbits, and monkeys, as is well known in the art.

Previously, certain phenylene-containing prostaglandin analogs were disclosed. See U.S. Pat. No. 3,933,897, 3,933,898, and 3,944,595, for a group of phenyleneoxa compounds having a divalent phenylene moiety

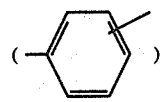

and an oxa oxygen (—O—) in the carboxyl-terminated side chain. See Belgian Pat. No. 820,003, Derwent Farmdoc 22475W for related compounds which are distinguishable from prostaglandins in that they are 11-deoxy compounds.

SUMMARY OF THE INVENTION

It is a purpose of this invention to provide novel phenylene prostaglandin analogs and intermediates and processes for making them.

The novel prostaglandin analogs of this invention each have a meta-substituted divalent phenylene moiety

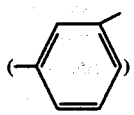

in the carboxyl-terminated side chain of the prostanoic acid structure (I). This phenylene group is in place of three of the six methylene portions of said chain.

For example, one of the novel prostaglandin analogs of this invention is represented by the formula:

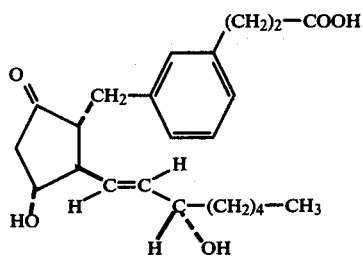

Based on its relationship to $PGE_1$ and prostanoic acid, the compound of formula V is named "4,5,6-trinor-3,7-inter-m-phenylene-$PGE_1$." This name is typical of the names used hereinafter, and is understood by reference to the structure and numbering system of prostanoic acid (formula I above).

The use of "trinor" in the names of the novel compounds of this invention indicates the absence of three of the chain carbon atoms and the attached hydrogen atoms. The numbers in front of "trinor" indicate which of the original prostanoic acid carbon atoms are missing in the named compound.

The numbers preceding the expression "inter-m-phenylene" indicate that m-phenylene has been inserted between the two carbon atoms so numbered in the formula of prostanoic acid.

Included among the novel inter-m-phenylene compounds of this invention are compounds represented by the formulas:

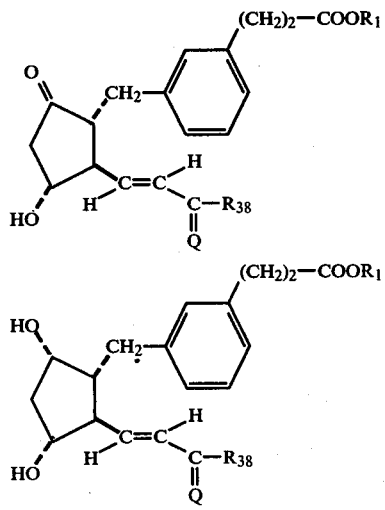

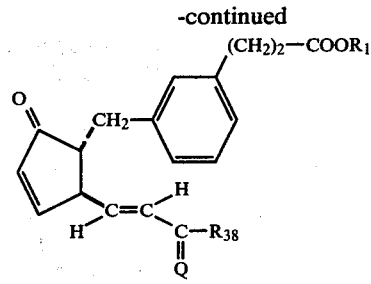

and the mixtures of those compounds and their respective enantiomers represented by the mirror images of the above formulas.

In formulas VI-VIII, Q is

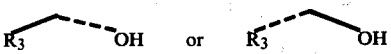

wherein $R_3$ is hydrogen or alkyl of one to 4 carbon atoms, inclusive; $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and $R_{38}$ is

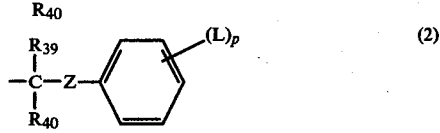

wherein $C_gH_{2g}$ is alkylene of one to 9 carbon atoms, inclusive, with one to 5 carbon atms, inclusive, in the chain between —$R_{39}R_{40}$— and terminal methyl, wherein $R_{39}$ and $R_{40}$ are hydrogen, alkyl of one to 4 carbon atoms, inclusive, or fluoro, being the same or different, with the proviso that one of $R_{39}$ and $R_{40}$ is fluoro only when the other is hydrogen or fluoro and the further proviso that neither $R_{39}$ nor $R_{40}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{39}R_{40}$- and the phenyl ring; and wherein L is alkyl of one to 4 carbon atoms, inclusive, fluoro, chloro, trifluoromethyl, or —$OR_{41}$— wherein $R_{41}$ is alkyl of one to 4 carbon atoms, inclusive, and p is zero, one, 2 or 3, with the proviso that not more than two L's are other than alkyl and when p is 2 or 3 the L's are either the same or different.

There are also included the pharmacologically acceptable salts when $R_1$ is hydrogen.

As in the case of formulas II to IV, formulas VI to VIII wherein Q is

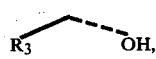

i.e. wherein the C-15 hydroxyl is attached to the side chain in alpha configuration, are each intended to represent optically active prostanoic acid derivatives with the same absolute configuration as PGE₁ obtained from mammalian tissues.

Also included within this invention are the 15-epimer compounds of formulas VI to VIII wherein Q is

These are identified hereinafter as "15-epi," "15β," or "15(R)" compounds by the appropriate prefix in the name. For example, "15-epi-4,5,6-trinor-3,7-inter-m-phenylene-PGE₁" identifies the 15-epimeric compound corresponding to the formula V example above except that it has the beta configuration at C-15 instead of the natural alpha configuration of 4,5,6-trinor-3,7-inter-m-phenylene-PGE₁. As is known in the art, "R" and "S" designation depends on the neighboring substituents. See R. S. Cahn, J. Chem. Ed. 41, 116 (1964).

The novel prostanoic acid derivatives of this invention also include the corresponding racemic compounds. Any one of formulas VI-VIII plus its mirror image is necessary in combination to describe a racemic compound. For convenience hereinafter, when the word "racemic" precedes the name of one of the novel prostanoic acid derivatives of this invention, the intent is to designate a racemic compound represented by the combination of the appropriate Formula VI-VIII and the mirror image of that formula. When the word "racemic" does not precede the compound name, the intent is to designate an optically active compound represented only by the appropriate Formula VI-VIII and with the same absolute configuration as PGE₁ obtained from animal tissues.

For convenience in the charts illustrating the transformations herein, only a single structural formula is used, for example in Chart A, to define not only the optically active form but also the racemic compound which generally undergoes the same reactions.

With regard to formulas VI to VIII, examples of alkyl of one to 4 carbon atoms, inclusive, are methyl, ethyl, propyl, butyl, and isomeric forms thereof. Examples of alkyl of one to 12 carbon atoms, inclusive, are those given above, and pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butyl-cyclopropyl, cyclobutyl, 2-methylcyclobutyl, 3-propyl-cyclobutyl, 2,3,4-triethylcyclobutyl, cyclopentyl, 2,2-dimethylcyclopentyl, 2-pentycyclopentyl, 3-tert-butyl-cyclopentyl, cyclohexyl, 4-tert-butylcyclohexyl, 3-siopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl or one to 4 carbon atoms, inclusive, are (o-, m-, or p-)chlorophenyl, 2,4-dichlorophenyl, 2,4,6-trichlorophenyl, (o-, m-, or p-)tolyl, p-ethylphenyl, p-tert-butylphenyl, 2,5-dimethylphenyl, 4-chloro-2-methylphenyl, and 2,4-dichloro-3-methylphenyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH₃)—, —C(CH₃)₂—, —CH(CH₂CH₃)—, —CH₂—CH(CH₃)—, —CH(CH₃)—CH(CH₃)—, —CH₂—C(CH₃)₂—, —CH₂—CH(CH₃)—CH₃—, —CH₂—CH₂—CH(CH₂CH₂CH₃)—, —CH(CH₃)—CH(CH₃)—CH₂—CH₂—, —CH₂—CH₂—CH₂—C(CH₃)₂—CH₂, and —CH₂—CH₂—CH₂—CH₂—CH(CH₃)—. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH₂—, —CHF—CHF—, —CH₂—CH₂—CF₂—, —CH₂—CHF—CH₂—, —CH₂—CH₂—CF(CH₃)—, —CH₂—CH₂—CF₂—CH₂—, —CH(CH₃)—CH₂—CH₂CHF—, —CH₂—CH₂—CH₂—CF₂—, —CHF—CH₂—CH₂—CH₂—CH₂—CHF—, —CF₂—CH₂—CH₂—CH₂—CH₂—CH₂—, —CH₂—CH₂—CH₂—CF₂—CH₂—CH₂—, and —CH₂—CH₂—CH₂—CH₂—CH₂—CF₂.

Examples of

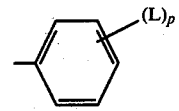

as defined above are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl, 4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2,4-dichloro(5- or 6-)methoxyphenyl.

Each of the novel prostaglandin analogs of formulas VI, VII, and VIII is useful in place of the above-mentioned kown prostaglandins for at least one of the pharmacological purposes known for the latter, and is surprisingly and unexpectedly more useful for that purpose because it has a different and narrower spectrum of biological activity than the known prostaglandin, and therefore is more specific in its activity and causes smaller and fewer undesired side effects that the known prostaglandin. Moreover, because of its prolonged activity, fewer and smaller doses of the novel prostaglandin analog can frequently be used to attain the desired result.

These novel PGE$_1$, PGF$_{1\alpha}$, and PGA$_1$ type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range 0.005 to about 20 mg. per kg. of body weight per day are used, the exact dose depending on the age, weight, and condition of the patient or animal, and on the frequency and route of administration.

These novel PGE$_1$-type analogs are useful as pypotensive agents to reduce blood pressure in mammals, including man. For this purpose the compounds are administered by intravenous infusion at the rate of about 0.01 to about 50 μg. per kg. of body weight per minute or in single or multiple doses of about 25 to 500 μg. per kg. of body weight total per day.

These inter-phenylene PG compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophylline); and corticosteroids (ACTH and predinisolone). Regarding use of these compounds see South African Patent No. 681,055.

The novel compounds of this invention have the further advantage that they are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

To obtain the optimum combination of biological response specificity, potency, and duration of activity, certain compounds within the scope of formulas VI to VIII are preferred. For example, it is preferred that Q be

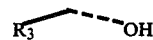

wherein R$_3$ is as defined above. It is especially preferred that R$_3$ be either hydrogen or methyl.

Another preference is, when R$_1$ is not hydrogen, that R$_1$ be alkyl of one to 12 carbon atoms, inclusive. It is further preferred that R$_1$ be alkyl of one to 4 carbon atoms, inclusive, and especially methyl or ethyl, for optimum absorption of the compound by the body or experimental animal system; and that R$_1$ be alkyl of 8 to 12 carbon atoms, inclusive, preferably straight-chain octyl, nonyl, decyl, undecyl, and dodecyl, for prolonged activity in the body or experimental animal.

It is further preferred that the sum of the number of carbon atoms in R$_3$, R$_{39}$, and R$_{40}$ be less than 7.

When R$_{38}$ is

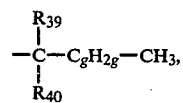

it is preferred that C$_g$H$_{2g}$ be alkylene of 2, 3, or 4 carbon atoms, and especially that it be trimethylene. It is further preferred that R$_{38}$ and R$_{40}$ be hydrogen, methyl, ethyl, or fluoro, being the same or different. It is further preferred, when R$_{39}$ and R$_{40}$ are not hydrogen, that both R$_{39}$ and R$_{40}$ be methyl or fluoro.

When R$_{38}$ is

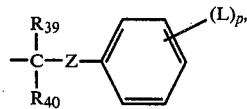

it is preferred that "p" be either zero or one. When "p" is not zero, it is preferred that L be methyl, chloro, fluoro, trifluoromethyl, or methoxy with meta or para attachment to the phenyl ring. When Z is oxa (—O—), it is preferred that R$_{39}$ and R$_{40}$ be hydrogen, methyl, or ethyl, being the same or different. It is further preferred, when R$_{39}$ and R$_{40}$ are not hydrogen, that both R$_{39}$ and $R_{40}$ be methyl. When Z is $C_jH_{2j}$, it is preferred that $C_jH_{2j}$ be a valence bond, methylene, or ethylene.

The inter-m-phenylene $PGE_1$, $PGF_{1\alpha}$, and $PGA_1$ compounds represented by formulas VI to VIII are used for the purposes described above in the free acid form, in ester form, or in pharmacologically acceptable salt form.

Pharmacologically acceptable salts of these formula VI–VIII compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amine-2-methyl-1-propanol, tris(hydroxymethyl)aminomethane, N-phenylethanolamine, N-(p-tert-amylphenyl)diethanolamine, galactamine, N-methylglucamine, N-methylglycosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of formula VI–VIII are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that $R_1$ in the formula VI–VIII compounds be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The inter-m-phenylene $PGE_1$, $PGF_{1\alpha}$, and $PGA_1$ type compounds encompassed by formulas VI–VIII are produced by the reactions and procedures described and exemplified hereinafter.

Reference to Charts A–G, herein will make clear the processes by which these novel compounds are produced.

CHART A

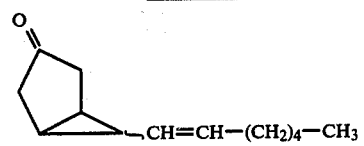

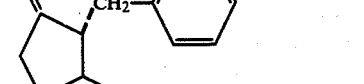

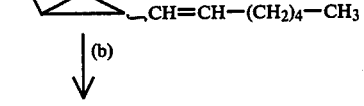

via alternate routes

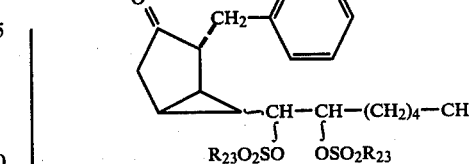

In Chart A are shown the steps of which the formula-IX bicyclo hexanone starting material is transformed to the inter-m-phenylene $PGE_1$-type product XIII. In Chart A, $Q_1$ is

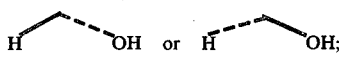

R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, $R_{23}$ is alkyl of one to 5 carbon atoms, inclusive; $R_{30}$ is alkyl of one to 4 carbon atoms, inclusive; and ~ indicates attachment of the side chain to the cyclopropane ring in endo or exo configuration and attachment to the side chain in alpha or beta configuration.

Bicyclo-ketone IX exists in four isomeric forms, exo and endo with respect to the attachment of the CH=CH—(CH₂)₄—CH₃ moiety, and cis and trans with respect to the double bond in that same moiety. Each of those isomers separately or various mixtures thereof are used as reactants according to this invention to produce substantially the same final interphenylene PGE₁ type product mixture.

The process for preparing either the exo or endo configuration of bicyclo-ketone IX is known to the art. As to the exo compound, see U.S. Pat. No. 3,776,940 and Belgian Pat. No. 702,477; reprinted in Farmdoc Complete Specifications, Bood 714, No. 30,905, page 313, Mar. 12, 1968. As to the endo compound, see German Offenlegungsschrift No. 1,937,912; reprinted in Farmdoc Complete Specifications, Book No. 14, No. 6869 R, Week R5, Mar. 18, 1970. See also U.S. Pat. No. 3,843,712.

In said U.S. Pat. No. 3,776,940, a reaction sequence capable of forming exo-ketone IX is as follows: The hydroxy group of 3-cyclopentenol is protected with a blocking group, for example tetrahydropyranyl or (α-ethoxy)ethyl. Then a diazoacetic acid ester is added to the double bond to give an exo-endo mixture of a bicyclo[3.1.0]hexane substituted at 3 with the protected hydroxy group and at 6 with an esterified carboxyl. The exo-endo mixture is treated with a base to isomerize the endo isomer in the mixture to more of the exo isomer. Next, the carboxylate ester group at 6 is transformed to an aldehyde group, —CHO. Then, said aldehyde group is transformed by the Wittig reaction to a moiety of the formula —CH=CH—(CH₂)₄—CH₃ which is in exo configuration relative to the bicyclo ring structure. Next, the blocking group is removed to regenerate the 3-hydroxy which is then oxidized, for example, by the Jones reagent, i.e. chromic acid (see J. Chem. Soc. 39 (1946)), to give said exo ketone IX.

Separation of the cis-exo and trans-exo isomers of IX is described in said U.S. Pat. No. 3,776,940. However, as mentioned above, that separation is usually not necessary since the cis-trans mixture is useful as a reactant in the next process step.

The process described in said U.S. Pat. No. 3,776,940 for producing the exo form of bicyclo-ketone IX uses as an intermediate, the exo form of a bicyclo[3.1.0]hexane substituted at 3 with a protected hydroxy group, e.g., tetrahydropyranyloxy, and at 6 with an esterified carboxyl. When the corresponding endo compound is substituted for that exo intermediate, the process in said Offenlegungsschrift No. 1,937,912 leads to the endo form of bicyclo-ketone IX. The endo compound to be used has the formula:

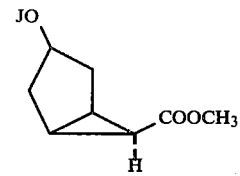

XIX wherein J represents a blocking group, for example tetrahydropyranyl or (α-ethoxy)ethyl. Compound XIX is prepared by reacting endo-bicyclo[3.1.0]hex-2-ene-6-carboxylic acid methyl ester with diborane in a mixture of tetrahydrofuran and diethyl ether, a reaction generally known in the art, to give endo bicyclo[3.1.0]hexan-3-ol-6-carboxylic acid methyl ester which is then reacted with the agent supplying the blocking group J, e.g., dihydropyran, in the presence of a catalytic amount of POCl₃ or other acid to give the desired compound. This is then used as described in said Offenlegungsschrift No. 1,937,912 to produce the endo form of bicyclo-ketone IX.

As with exo IX, this process produces a mixture of endo-cis and endo-trans compounds. These are separated as described for the separation of exo-cis and exo-trans IX, but this separation is usually not necessary since, as mentioned above, the cis-trans mixture is useful as a reactant in the next process step.

Further exemplification of the source of endo bicyclo-ketone IX is found in U.S. Pat. No. 3,843,712 at columns 23–24, and 30–32, said portions of referenced patent being incorporated herewith by reference under the provisions of M.P.E.P. 608.01(p).

Continuing with Chart A, in step (a) starting material IX is alkylated to form bicyclo-ketone-olefin X. The alkylating agent is a haloester of the formula

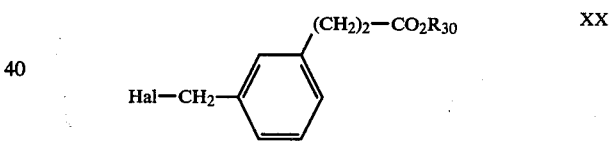

XX wherein Hal is chloro, bromo, or iodo, and $R_{30}$ is alkyl of one to 4 carbon atoms, inclusive. Such alkylating agents are readily available or prepared by methods known in the art. For example, herein in Preparations 1 and 2, 3-(m-bromomethyl)phenyl propionate, methyl ester is obtained by the series of reactions:

XXI

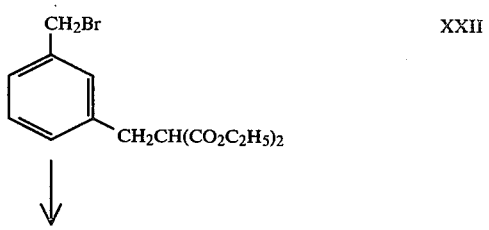

XXII

-continued

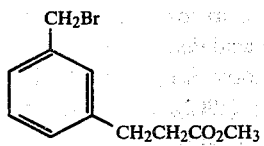
XXIII

Thus, compound XXII is formed by a malonic ester synthesis and subsequently decarboxylated to the substituted propionate XXIII. Other esters within the scope of $R_{30}$ are readily prepared.

Any of the alkylation procedures known in the art to be useful for alkylating cyclic ketones with alkyl halides and haloalkanoic esters are used for the transformation of IX to X. See, for example, the above-mentioned U.S. Pat. No. 3,776,940 for procedures useful here and used there to carry out similar alkylations.

For these alkylations, it is preferred that Hal be bromo or iodo. Any of the usual alkylation bases, e.g., alkali metal alkoxides, alkali metal amides, and alkali metal hydrides, are useful for this alkylation. Alkali metal alkoxides are preferred, especially tert-alkoxides. Sodium and potassium are preferred alkali metals. Expecially preferred is potassium tert-butoxide. Preferred diluents for this alkylation are tetrahydrofuran and 1,2-dimethoxyethane. Otherwise, procedures for producing and isolating the desired formula X compounds are within the skill of the art.

These alkylation procedures produce mixtures of alpha and beta alkylation products, i.e., a mixture of formula X products wherein part has the

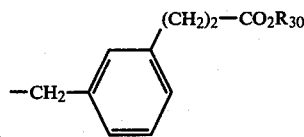

moiety attached in alpha configuration, and wherein part has that moiety attached in beta configuration. When about one equivalent of base per equivalent of formula IX ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Chart A. Silica gel chromatography is preferred for this separation.

Concerning the alkylation of compound IX (Chart A), another useful alkylation procedure utilizes an intermediate enamine. That enamine is prepared by mixing the formula-IX bicyclo-ketone with a secondary amine of the formula

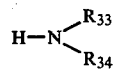

wherein $R_{33}$ and $R_{34}$ are alkyl or alkylene linked together through carbon or oxygen to form together with a nitrogen a 5 to 7-membered heterocyclic ring. Examples of suitable amines are diethylamine, dipropylamine, dibutylamine, dihexylamine, dioctylamine, dicyclohexylamine, methylcyclohexylamine, pyrrolidine, 2-methylpyrrolidine, piperidine, 4-methylpiperidine, morpholine, hexamethylenimine, and the like.

The enamine is prepared by heating a mixture of the formula-IX compound with an excess of the amine, if desired in the presence of a strong acid catalyst such as an organic sulfonic acid, e.g., p-toluenesulfonic acid, or an inorganic acid, e.g., sulfuric acid. It is advantageous to carry out this reaction in the presence of a water-immiscible diluent, e.g., benzene or toluene, and to remove water by azeotropic distillation as it is formed during the reaction. Then, after water formation ceases, the enamine is isolated by conventional methods.

The enamine is then reacted with a haloester of the formula

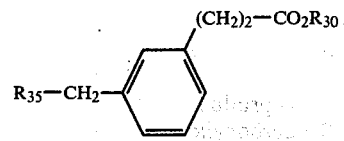

wherein $R_{30}$ is as defined above to give the desired formula-X intermediate. In addition to halogen, $R_{35}$ can also be tosylate, mesylate, and the like. It is especially preferred that $R_{35}$ be bromine or iodine. Dimethylsulfoxide is especially useful as a diluent in the reaction of the enamine with the haloester. This reaction of the enamine is carried out by the usual procedures. See "Advances in Organic Chemistry," Interscience Publishers, New York, N.Y., Vol. 4, pp. 25–47 (1963) and references cited therein.

The transformation of bicyclo-ketone-olefin X to glycol XI is carried out by reacting olefin X with a hydroxylation reagent. Hydroxylation reagents and procedures for this purpose are known in the art. See, for example, Gunstone, Advances in Organic Chemistry, Vol. 1, pp. 103–147, Intersicence Publishers, New York, N.Y. (1960). Various isomeric glycols are obtained depending on such factors as whether olefin X is cis or trans and endo or exo, and whether a cis or a trans hydroxylation reagent is used. However, all of the isomeric formula XI erythro and threo glycols and the various glycol mixtures each are useful as an intermediate according to this invention and the processes of Chart A to produce final products of Formula XIII. Therefore, it is usually not necessary to separate individual glycol XI isomers before proceeding further in the synthesis, although that separation is accomplished by silica gel chromatography.

Referring again to Chart A, one of the alternate routes from XI to XIII is by hydrolysis of bis-alkanesulfonic acid esters. Other routes include formolysis and use of a cyclic ortho ester and will be discussed below. The bis-alkanesulfonic acid esters XII are prepared by reacting glycols XI with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25° C. for several hours. The formula XII bis-sulfonic acid esters are then isolated by procedures known to the art.

The transformation of XII to the PGE type compounds XIII are carried out by reacting bis-esters XII with water in the range about 0° to about 60° C. In making the interphenylene PGE$_1$ compounds, 25° C. is a suitable reaction temperature, the reaction then proceeding to completion in about 5 to 20 hours. This is accomplished by adding sufficient of a water-soluble organic diluent which does not enter into the reaction. Acetone is a suitable diluent. The desired product is isolated following evaporation of excess water and diluent if one is used. The residue contains a mixture of formula XIII isomers which differ in the configuration of the side chain hydroxy, that being either alpha (S) or beta (R). These are separated from byproducts and from each other by silica gel chromatography.

For the transformations of bis-sulfonic acid esters XII to final products XIII, it is preferred to use the bis-mesyl esters, i.e., compounds XII wherein $R_{23}$ is methyl.

The solvolysis products from bis-sulfonic acid esters XII are all $R_{30}$ carboxylic acid esters, wherein $R_{30}$ is as defined above. For some of the uses described above, it is preferred that the novel formula-VI inter-phenylene prostaglandin-like compounds of this invention be in free acid form, or in salt form which requires the free acid as a starting material. The PGF-type esters of formula VII, which are prepared from PGE-type esters of formula VI as will be hereinafter disclosed, are easily hydrolyzed or saponified to the free acids by the usual known procedures, especially when $R_1$ ($R_{30}$) is alkyl of one to 4 carbon atoms, inclusive, preferably methyl or ethyl.

On the other hand, the PGE-type esters are difficult to hydrolyze or saponify without causing unwanted structural changes in the desired acids. There are at least two other procedures to make the free acid forms of these formula VI PGE-type compounds.

One of those procedures is applicable mainly in preparing the free acids from the corresponding alkyl esters wherein the alkyl group contains one to 8 carbon atoms, inclusive. That procedure comprises subjecting the PG-type alkyl ester to the acylase enzyme system of a microorganism species of Subphylum 2 to Phylum III, and thereafter isolating the acid. See West Germany Offenlegungsschrift No. 1,937,678; reprinted in Farmdoc Complete Specifications, Book No. 13, No. 6863 R, Week R5, Mar. 18, 1970.

Another procedure for making the free acids of formula VI PGE-type compounds involves treatment of certain haloethyl esters of those acids with zinc metal and an alkanoic acid of 2 to 6 carbon atoms, preferably acetic acid. The procedure employed is described in U.S. Pat. No. 3,843,712 at columns 18–19 and 25–29, which material is incorporated by reference herein; those reactants and intermediates being necessarily replaced with the appropriate intermediates herein containing an inter-phenylene carboxyl-terminated side chain.

Still another procedure is to (a) reduce a PGE-type ($R_{30}$) ester to a PGF$_1$-type ($R_{30}$) ester, (b) saponify the latter to obtain the free acid, (c) optionally esterify with a group other than $R_{30}$, for example phenyl, and (d) oxidize the resulting PGF$_1$-type ($R_1$) compound, either free acid or ester, to the corresponding PGE$_1$-type ($R_1$) compound.

The transformation of formula-V: inter-phenylene PGE$_1$-type compounds to formula-VII inter-phenylene PGF$_{1\alpha}$-type compounds is done by carbonyl reduction.

These ring carbonyl reductions are carried out by methods known in the art for ring carbonyl reductions of known prostanoic acid derivatives. See, for example, Bergstrom et al., Arkiv Kemi 19, 563 (1963), Acta Chem. Scand. 16, 969 (1962), and British Specification No. 1,097,533. Any reducing agent is used which does not react with carbon-carbon double bonds or ester groups. Preferred reagents are lithium (tri-tert-butoxy) aluminum hydride, the metal borohydrides, e.g., sodium, potassium and zinc borohydrides and metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See for example, Bergstrom et al., cited above, Granstrom et al., J. Biol. Chem. 240, 457 (1965), and Green et al., J. Lipid Research 5, 117 (1964). Especially preferred as separation methods are column or partition chromatographic procedures, both normal and reversed phase, preparative thin layer chromatography, and countercurent distribution procedures.

In Chart B is shown a preferred method for transforming the PGE$_1$-type compounds to PGF$_{1\alpha}$-type compounds. Higher yields of the alpha isomers result by this method. In step (a) there is formed a silylated derivative wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms inclusive, and wherein $R_{31}$ is hydrogen or —Si(A)$_3$ when $R_1$ in the formula —VII product is to be hydrogen, or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive.

In Chart B, Q is

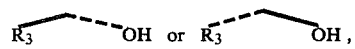

wherein $R_3$ is hydrogen or alkyl of one to 4 carbon atoms, inclusive; and $Q_2$ is

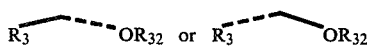

wherein $R_{32}$ is hydrogen or —Si(A)$_3$.

CHART B

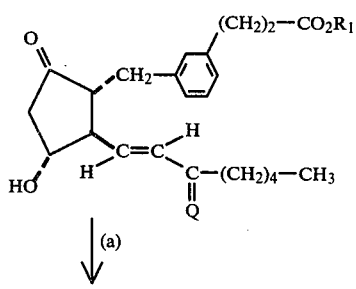

-continued
CHART B

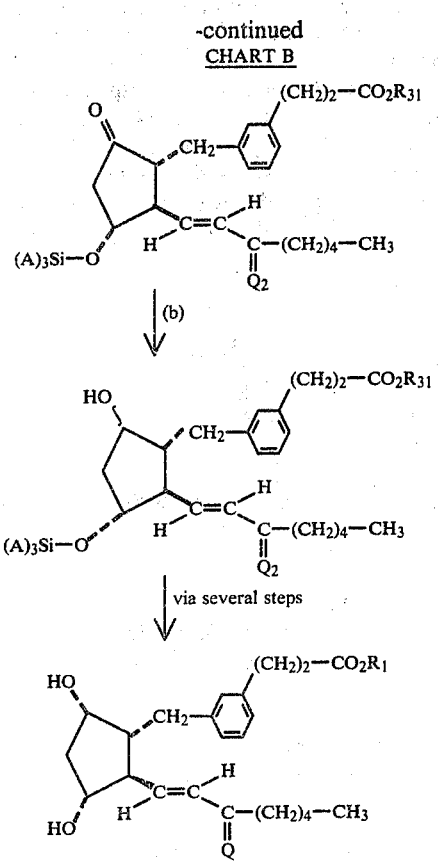

In step (b) di- or trisilylated intermediate XIV is reduced to intermediate XV which is usually a mixture of the 9α and 9β isomers. In subsequent steps, compound XV is hydrolyzed to the corresponding formula-VII PGF$_{1\alpha}$-type acids and esters which are separated from the minor amount of co-formed PGF$_{1\beta}$-type compounds. Details of this process are available from U.S. Pat. No. 3,651,116, columns 1-10, which are incorporated herein by reference; those reactants and intermediates being necessarily replaced with the appropriate reactants and intermediates herein containing an inter-phenylene caarboxyl-terminated side chain.

Alternately, the PGF$_{1\alpha}$-type products of this invention are obtained from the PGE$_1$-type compounds by reduction with bulky trialkyl borohydride reagents (See E. J. Corey et al. J. Am. Chem. Soc. 93, 7319 (1971)) represented by the formulas

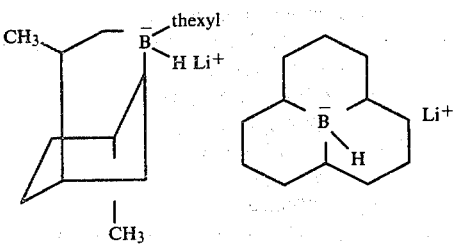

In Chart C are shown the steps for preparing 15-alkyl inter-phenylene PGF$_{1\alpha}$ compounds, using as starting material inter-phenylene PGF$_{1\alpha}$ compounds XVI in which Q$_1$ is

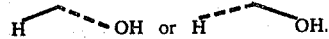

These are available from the PGE$_1$-type compounds XIII of Chart A by reduction as described above.

CHART C

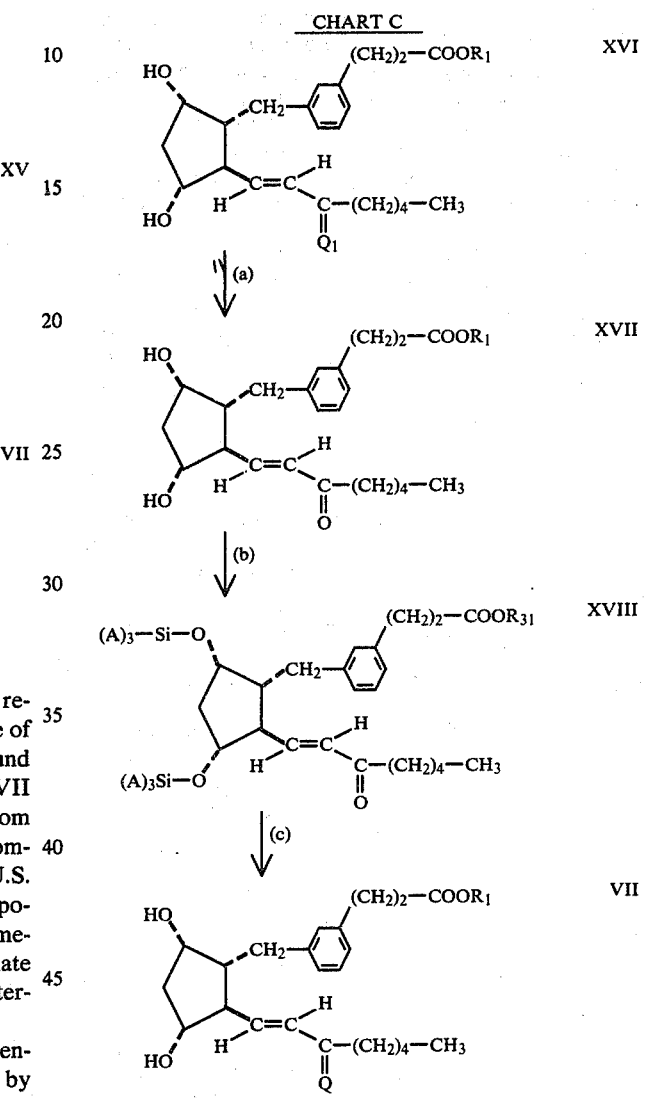

In Chart C, symbols A, Q, R$_1$, and R$_{31}$ are as defined above.

In step (a) of Chart C the formula-XVII 15-oxo acids and esters are formed from acids and esters of formula XVI by oxidation with reagents such as 2,3-dichloro-5,6-dicyano-1,4-benzoquinone, activated manganese dioxide, or nickel peroxide (see Fieser et al., "Reagents for Organic Synthesis," pp. 215, 637, and 731). Alternatively, these oxidations are carried out by oxygenation in the presence of the 15-hydroxy-prostaglandin dehydrogenase of swine lung (see Arkiv. för Kemi 25, 293 (1966)). These reagents are used according to procedures known in the art. See, for example, J. Biol. Chem. 239, 4097 (1964).

In step (b) of Chart C, intermediate compounds XVII are transformed to silyl derivatives XVIII by procedures known in the art. See, for example, Pierce, "Silylation of Organic Compounds," Pierce Chemical Co., Rockford, Ill. (1968). Both hydroxy groups of the formula XVII reactants are thereby transformed to —O—Si—(A)$_3$ moieties wherein A is as defined above, and sufficient of the silylating agent is used for that purpose according to known procedures. When $R_1$ in intermediate XVII is hydrogen, the —COOH moiety thereby defined is simultaneously transformed to —COO—Si—(A)$_3$ additional silylating agent being used for this purpose. This latter transformation is aided by excess silylating agent and prolonged treatment. When $R_1$ in formula XVII is alkyl, then $R_{31}$ in formula XVIII will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

In step (c) of Chart C, intermediate silyl compounds XVIII are transformed to the final compounds of formulas VII by first reacting the silyl compound with a Grignard reagent of the formula $R_{30}$MgHal wherein $R_{30}$ is alkyl of one to 4 carbon atoms, inclusive, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantgeous to use a mixture of water and sufficient of a water-miscilbe solvent, e.g., ethanol to give a homogeneous reaction mixture. The hydrolysis is usually complete in 2 to 6 hours at 25° C. and is preferably carried out in an atmosphere of an inert gas, e.g., nitrogen or argon.

The mixture of 15α- and 15β-isomers obtained by this Grignard reaction and hydrolysis is separated by procedures known in the art for separating mixtures of prostanoic acid derivatives, for example, by chromatography on silica gel. In some instances, the lower alkyl esters, especially the methyl esters of a pair of 15α- and 15β- isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

In Chart D are shown the inter-conversions between the PGE$_1$-, PGF$_{1\alpha}$-, and PGA$_1$-type products of this invention. Thus, in step (a), a PGE$_1$-type compound of formula VI is transformed into a PGF$_{1\alpha}$-type compound of formula VII. Two methods for this transformation were discussed above. In Chart D, Q and $R_1$ are as defined above.

In step (b), a PGF$_{1\alpha}$-type compound is transformed into a PGE$_1$-type compound by oxidation. For this purpose, an oxidizing agent is used which selectively oxidizes secondary hydroxy groups to carbonyl groups in the presence of carbon carbon double bonds. The PGF$_{1\alpha}$-type isomers are shown in Chart D to yield PGE$_1$-type compounds but mixtures of PGF$_{1\alpha}$-and PGF$_{1\beta}$-type isomers are also useful for preparing PGE$_1$ type products.

Oxidation reagents useful for this transformation are known to the art. An especially useful reagent for this purpose is the Jones reagent, i.e., acidified chromic acid See J. Chem. Soc. 39 (1946). Acetone is a suitable diluent for this purpose, and a slight excess beyond the amount necessary to oxidize one of the secondary hydroxy groups of the 15-alkyl PGF reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the PGE-type product is isolated by conventional methods.

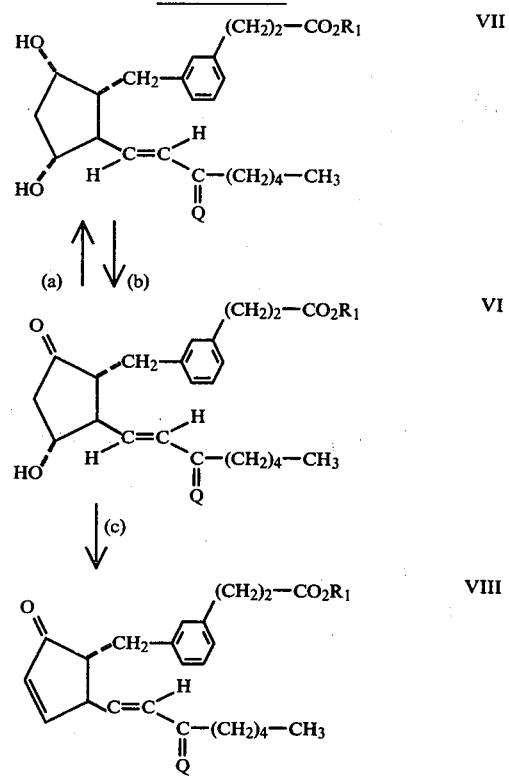

CHART D

Examples of other oxidation reagents useful for this purpose are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexyl-carbodiimide and dimethyl sulfoxide (J. Am. Chem. Soc. 87, 5661 (1965)).

For the transformation of these PGF$_{1\alpha}$-type compounds to PGE$_1$-type compounds, a preferred method is by way of silylated intermediates. Details of this process are available from U.S. Pat. No. 3,892,792, columns 5–17, which are incorporated herewith by reference; the PGF$_{2\alpha}$-type compound of that disclosure are replaced with the appropriate interphenylene PGF$_{1\alpha}$-type compounds of this invention.

In step (c), a PGE$_1$-type compound is transformed into a PGA$_1$-type compound by acidic dehydration. These acidic dehydrations are carried out by methods known in the art for acidic dehydrations of known prostanoic acid derivative See, for example, Pike et al., Proc. Nobel Symposium II. Stockholm (1966); Interscience Publishers, New York, pp. 162–163 (1967), British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent e.g., tetrahydrofuran, are also useful as reagents for the acidic dehydration, although these reagents may also cause partial hydrolysis of an ester reactant.

Alternately, the PGE$_1$-type compound is transformed to a bis-trifluoroacetate, for example by reaction with trifluoroacetic anhydride in the presence of pyridine in a solvent at 0° to 5° C., and thereafter contacted with a low-boiling alcohol (preferably b.p. below 110° C.) with a tertiary amine to form a PGA$_1$-type compound.

The PGA$_1$-type product is isolated by methods known in the art, e.g., filtration of the reaction mixture and evaporation of the filtrate. If desired, the product is purified by methods known in the art, advantageously by chromatography on silica gel.

An alternate method of synthesis for the inter-m-phenylene prostaglandin E$_1$ and F$_{1\alpha}$ analogs of this invention is provided hereinafter, utilizing oxetane intermediates of the formula

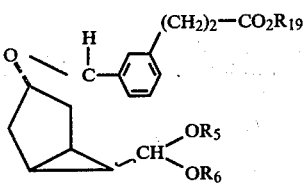

LXIII wherein R$_5$ and R$_6$ are alkyl of one to 4 carbon atoms, inclusive, or, when taken together,

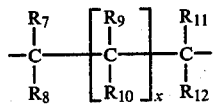

wherein R$_7$, R$_8$, R$_9$, R$_{10}$, R$_{11}$, and R$_{12}$ are hydrogen, alkyl of one to 4 carbon atoms, inclusive, or phenyl, with the proviso that not more than one of the R's is phenyl and the total number of carbon atoms is from 2 to 10, inclusive, x is zero or one; wherein R$_{19}$ is hydrogen or alkyl of one to 4 carbon atoms, inclusive; and wherein ~ indicates attachment to the cyclopropane ring in endo or exo configuration.

Reference to Charts E and F will make clear the steps by which starting material XXX is transformed to products LXXII and LXXV. The formula-XXX compound wherein R$_5$ and R$_6$ together are —CH$_2$—C(CH$_3$)$_2$—CH$_2$— and ~ is endo, i.e. bicyclo [3.1.0]hex-2-ene-6-endo-carboxaldehyde neopentyl glycol acetal, is available either in racemic or optically active form. See U.S. Pat. No. 3,711,515 for both the endo and exo forms, either of which will yield the ultimate analogs of formula LXXII by the processes of Chart E. In Charts E and F, the symbols Q, R$_1$, R$_3$, and ~ have the same meanings as for Charts A-D above. R$_{16}$ is hydrogen or a blocking group R$_{15}$ as further defined below. R$_{18}$ represents hydrogen. carboxyacyl R$_{13}$ represented by the formula

wherein R$_{14}$ is hydrogen, alkyl of one to 19 carbon atoms, inclusive, or aralkyl of 7 to 12 carbon atoms, inclusive, wherein alkyl or aralkyl are substituted with zero to 3 halo atoms; benzoyl and substituted benzoyl as represented by

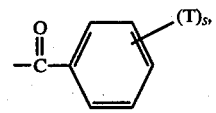

wherein T is alkyl of one to 4 carbon atoms, inclusive, phenylalkyl of 7 to 10 carbon atoms, inclusive, or nitro, and s is zero to 5, inclusive, provide that not more than two T's are other than alkyl and that the total number of carbon atoms in the T's does not exceed 10 carbon atoms; mono-esterified phthaloyl as represented by

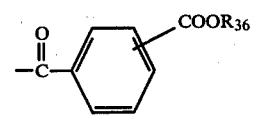

wherein R$_{36}$ is alkyl of one to 4 carbon atoms, inclusive; or naphthoyl and substituted naphthoyl as represented by

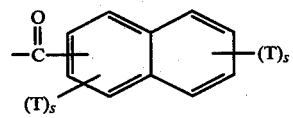

wherein T and s are as defined above. R$_{19}$ is hydrogen or alkyl of one to 4 carbon atoms, inclusive, and R$_{20}$ is hydrogen, alkyl of one to 4 carbon atoms, inclusive, or silyl of the formula (A)$_3$Si— wherein A is as defined for Chart B. In Charts E and F, as in the other charts of this specification the formulas as drawn represent specific optical isomers following the conventions applied herein to the end products. However, for purposes of convenience and brevity it is intended that such representations of the process steps for the optically active intermediates are applicable to those same process steps as used for the corresponding racemic intermediates.

CHART E

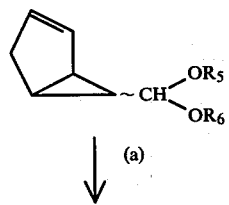

XXX

↓ (a)

-continued
CHART E
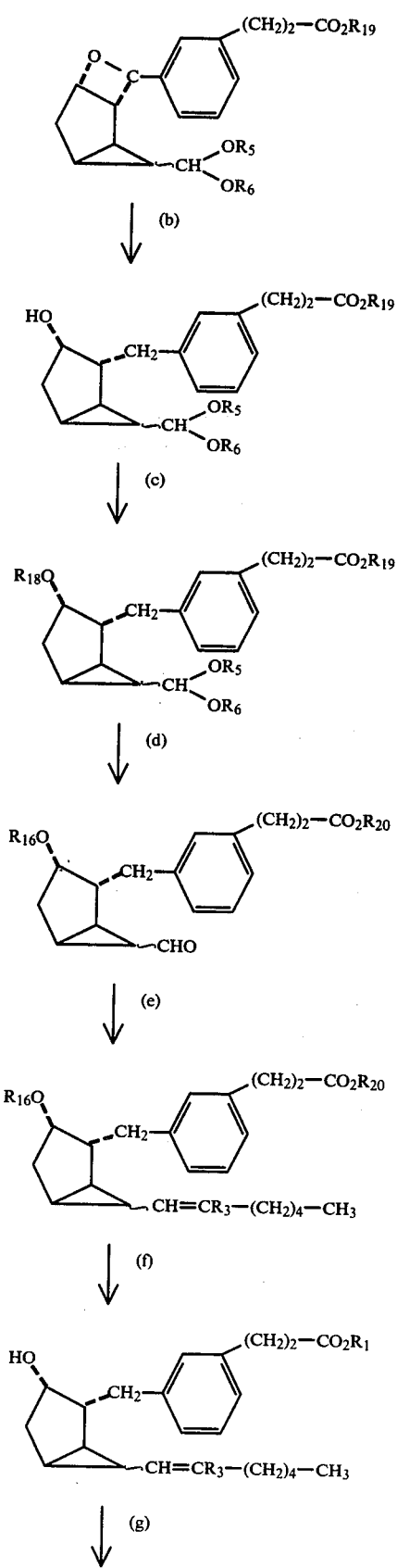
-continued
CHART E
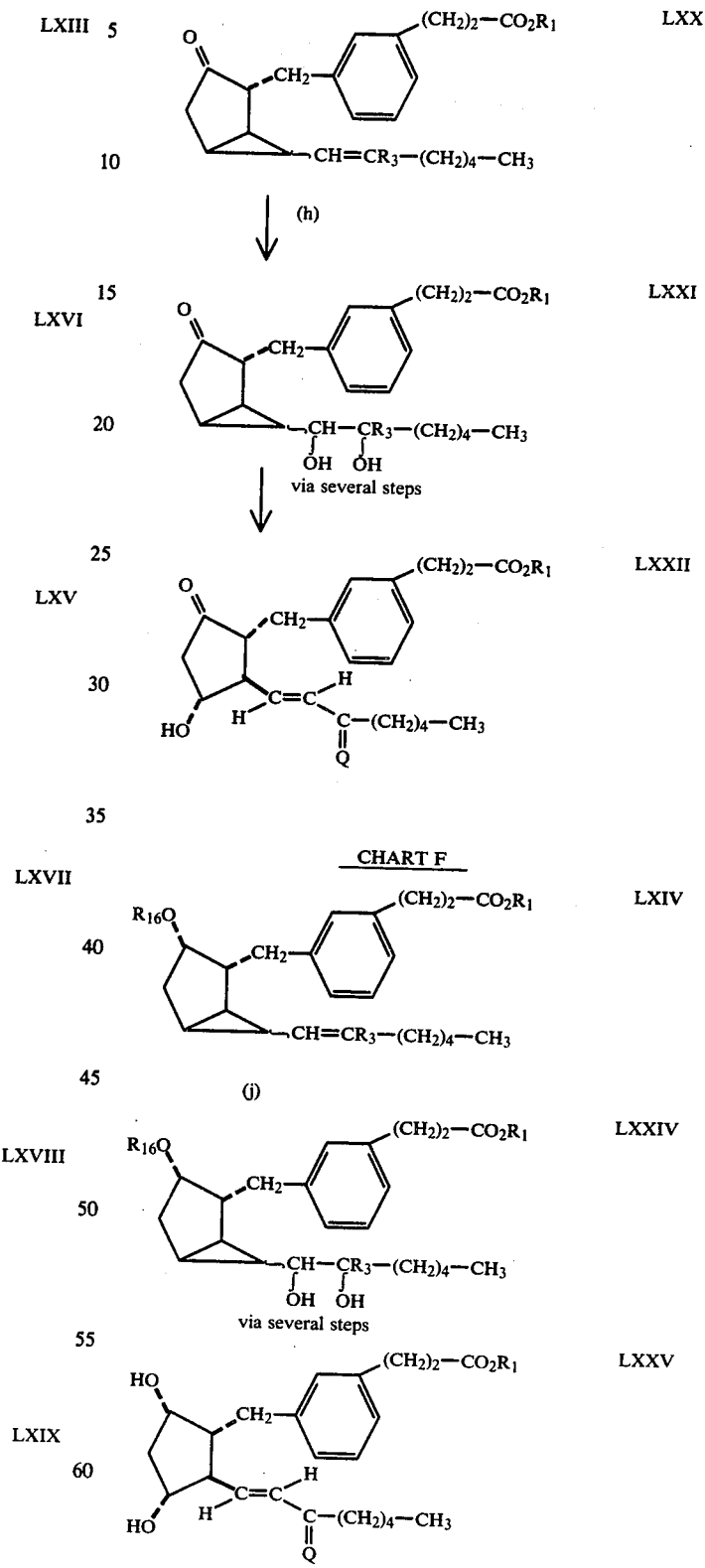
Referring to Chart E, in step (a) oxetane LXIII is obtained by reaction of the formula-XXX bicyclic hexene with an aldehyde of the formula

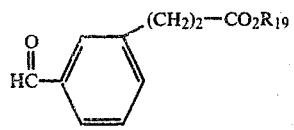  LXXXI wherein $R_{19}$ is as defined above. Such aldehydes are available or readily prepared by methods known in the art. Chart G summarizes the steps employed herein (See Preparations 4-8 for the preparation of (m-formylphenyl)propionate, methyl ester).

The formation of oxetane LXIII is accomplished by photolysis of a mixture of bicyclo hexene XXX and the aldehyde in a solvent. The bicyclo hexene is preferably used in excess over the molar equivalent, for example 2 to 4 times the theoretical equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78° C. to the boiling point of the solvent. The irradiation is done with mercury vapor lamps of the low or medium pressure type, for example those peaking at 3500 Å. Such sources are available from The Southern New England Ultraviolet Co., Middletown, Conn. Alternatively, those lamps which emit a broad spectrum of wavelengths and which may be filtered to transmit only light of $\lambda \sim 3000\text{-}3700$ Å may also be used. For a review of photolysis see D. R. Arnold in "Advances in Photochemistry," Vol. 6, W. A. Noyes et al., Wiley-Interscience, New York, 1968, pp. 301-423.

In step (b) the cleavage of the oxetane ring to yield the formula-LXVI compounds is accomplished with an alkali metal in the presence of a primary amine or alcohol. Preferred is lithium in ethylamine, or sodium in ethyl alcohol. See L. J. Altman et al., Synthesis 129 (1974).

CHART G

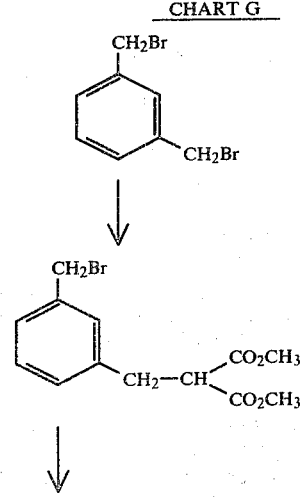

LXXVI

LXXVII

-continued
CHART G

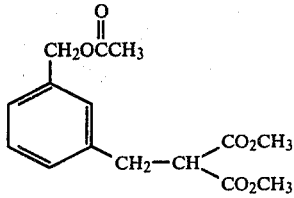  LXXVIII

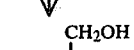

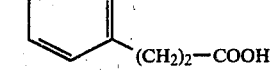  LXXIX

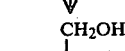  LXXX

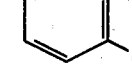

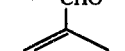  LXXXI

The cleavage transformation may also be accomplished by catalytic hydrogenation over an inert metal catalyst, e.g. Pd on carbon, in ethyl acetate or ethanol.

In step (c) compounds LXVI are prepared for step (d) by preferably blocking the hydroxyl groups with carboxyacyl groups within the scope of $R_{13}$ as defined above, i.e. $R_{14}C(O)$-. For example, LXVI is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{14}C(O)Cl$, $R_{14}C(O)Br$, or $R_{14}C(O)F$ and carboxyacid anhydrides.

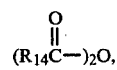

wherein $R_{14}$ is as defined above. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, stearic anhydride, (mono, di, or tri) chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, and phenoxyacetic anhydride. The choice of anhydride depends upon the identity of $R_{14}$ in the final acylated product, for example when $R_{14}$ is to be methyl, acetic anhydride is used; when $R_{14}$ is to be 2-chlorobutyl, 3-chlorovaleric anhydride is used.

When $R_{14}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, compound LXVI is reacted with two equivalents of sodium hydride and then with excess ethyl formate.

In formula LXV, $R_{18}$ may also represent an aromatic group such as benzoyl, substituted benzoyl, monoesterified phthaloyl, naphthoyl and substituted naphthoyl. For introducing those blocking groups, methods known in the art are used. Thus, an aromatic acid of the formula $R_{18}OH$, wherein $R_{18}$ is as defined above, for example benzoic acid, is reacted with the formula-LXVI compound in the presence of a dehydration agent, e.g. sulfuric acid, zinc chloride, or phosphoryl chloride; or an anhydride of the aromatic acid of the formula $(R_{18})_2O$, for example benzoic anhydride, is used.

As examples of reagents providing $R_{18}$ for the purposes of this invention, the following are available as acids ($R_{18}OH$), anhydrides (($R_{18})_2O$), or acyl chlorides ($R_{18}Cl$): benzoyl; substituted benzoyl, e.g. (2-, 3-, or 4-)methylbenzoyl, (2-, 3-, or 4-)ethylbenzoyl, (2-, 3-, or 4-)isopropylbenzoyl, (2-, 3-, or 4-)tert-butyl-benzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-(toluyl, 2-, 3-, or 4-) 4-phenethyl-benzoyl, 2-, 3-, or 4-nitrobenzoyl, (2,4-, 2,5-, or 3,5-)dinitrobenzoyl, 4,5-dimethyl-2-nitrobenzoyl, 2-nitro-6-phenethylbenzoyl, 3-nitro-2-phenethylbenzoyl; monoesterified phthaloyl, e.g.

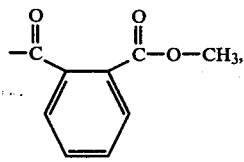

isophthaloyl, e.g.

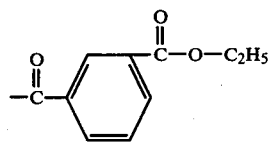

or terephthaloyl, e.g.

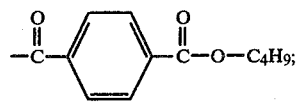

(1- or 2-)naphthoyl; and substituted naphthoyl, e.g. (2-, 3-, 4-, 5-, 6-, 7-)-methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7- or 8-)-methyl-1-naphthoyl, 4-ethyl-2-naphthoyl, and (5- or 8-)-nitro-2-naphthoyl.

Examples of aromatic acid anhydrides useful for this purpose are benzoic anhydride, (o, m, or p)-bromobenzoic anhydride, 2,4 (or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 4)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride.

Preferably, however, an acyl halide, e.g. $R_{18}Cl$, for example benzoyl chloride, is reacted with the formula-LXVI compound in the presence of a tertiary amine such as pyridine, triethylamine, and the like. The reaction is carried out under a variety of conditions using procedures generally known in the art. Generally, milk conditions are employed, e.g. 20°-60° C., contacting the reactants in a liquid medium, e.g. excess pyridine or an inert solvent such as benzene, toluene or chloroform. The acylating agent is used either in stoichiometric amount or in excess. There may be employed, therefore, benzoyl chloride, 4-nitrobenzoyl chloride, 3,5-dinitrobenzoyl chloride, and the like, i.e. $R_{18}Cl$ compounds corresponding to the above $R_{18}$ groups. If the acyl chloride is not available, it is made from the corresponding acid and phosphorus pentachloride as is known in the art.

In step (d), the formula-LXV acetal is converted to aldehyde LXVII by acid hydrolysis, known in the art, using dilute mineral acids, acetic or formic acids, and the like. Solvents such as acetone, dioxane, and tetrahydrofuran are used.

For steps (e) through (h) it is optional whether $R_{16}$ be hydrogen or a "blocking group" as defined below. For efficient utilization of the Wittig reagent it is preferred that $R_{16}$ be a blocking group. If the formula-LXV compound is used wherein $R_{18}$ is hydrogen, the formula-LXVII intermediate will have hydrogen at $R_{16}$. If $R_{16}$ is to be a blocking group, that may be readily provided prior to step (e) by reaction with suitable reagents as discussed below.

The blocking group, $R_{15}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{13}$ above, i.e. acetyl, and also benzoyl, naphthoyl, and the like; (b) tetrahydropyranyl; (c) tetrahydrofuranyl; (d) a group of the formula

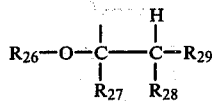

wherein $R_{26}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{27}$ and $R_{28}$ are the same or different, being hydrogen, alkyl of one to 4 carbon atoms, inclusive, phenyl or phenyl substituted with one, 2, or 3 alkyl of one to 4 carbon atoms, inclusive, or, when $R_{27}$ and $R_{28}$ are taken together, $-(CH_2)_a-$ or $-(CH_2)_b-O-(CH_2)_c-$ wherein a is 3, 4, or 5, b is one, 2, or 3, and c is one, 2, or 3 with the proviso that b plus c is 2, 3, or 4, and wherein $R_{29}$ is hydrogen or phenyl; or (e) $-Si(A)_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

In replacing the hydrogen atoms of the hydroxyl groups with carboxyacyl, benzoyl, naphthoyl, etc. blocking groups, methods known in the art are used. The reagents and conditions are discussed above for $R_{18}$ on compound LXVI.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

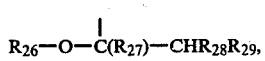

as defined above, the appropriate reagent is a vinyl ether, e.g. isobutyl vinyl ether or any vinyl ether of the formula $R_{26}-O-C(R_{27})=CR_{28}R_{29}$ wherein $R_{26}$, $R_{27}$, $R_{28}$, and $R_{29}$ are as defined above; or an unsaturated cyclic or heterocyclic compound, e.g. 1-cyclohex-1-yl methyl ether

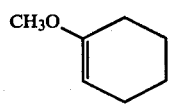

or 5,6-dihydro-4-methoxy-2H-pyran

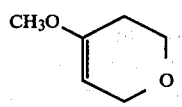

See C. B. Reese et al., J. Am. Chem. Soc. 89, 3366 (1967). The reaction conditions for such vinyl ethers and unsaturates are similar to those for dihydropyran above.

When the blocking group is silyl of the formula $-Si(A)_3$, the formula-XXI compound is transformed to a silyl derivative of formula LXVII by procedures known in the art. See, for example, Pierce, "Silylation of Organic Compounds," Pierce Chemical Co., Rockford, Ill. (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents suitable for forming the formula-XXI intermediates include pentamethylsilylamine, pentaethylsilylamine, N-trimethylsilydiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In step (e) the aldehyde group is transformed by the Wittig reaction to a moiety of the formula $-CH=C-R_3-(CH_2)_4-CH_3$ wherein $R_3$ is hydrogen or alkyl of one to 4 carbon atoms, inclusive. For this purpose a phosphonium salt prepared from an organic chloride or bromide of the formula

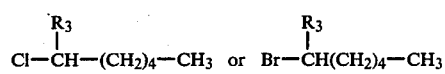

is employed, wherein $R_3$ is as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

In step (f) compound LXIX is obtained by deblocking if $R_{16}$ is a blocking group on LXVIII.

Total hydrolysis of $R_{16}$ blocking groups on compound LXVIII is accomplished, when $R_{16}$ is carboxyacyl, with an alkali alkoxide in an alcoholic solvent, preferably sodium methoxide in methanol at a temperature from 25° C. to reflux. When $R_{16}$ is tetrahydropyranyl, aqueous acid, e.g. dilute acetic acid, is used at 25° to 50° C. When $R_{16}$ is trialkylsilyl, either aqueous acid or base are used at 25° to 50° C.

Referring to step (g) of Chart E, the hydroxyl on the cyclopentane ring at the C-9 position is oxidized to an oxo group.

Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize the C-9 secondary hydroxy groups of the formula-LXIX reactant is used. Acetone is a suitable diluent for this purpose. Reaction temperatures at least as low as about 0° C. should be used. Preferred reaction temperatures are in the range 0° to −50° C. Another useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

Examples of other oxidation reagents useful for this transformation are silver carbonate on Celite (Chem. Commun. 1102 (1969)), mixtures of chromium trioxide and pyridine (J. Am. Chem. Soc. 75, 422 (1953), and Tetrahedron, 18, 1351 (1962)), t-butylchromate in pyridine (Biochem. J. 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

The transformation from compound LXX to product LXXII may be accomplished by any of several routes known in the art. See U.S. Pat. No. 3,711,515. Thus, by step (h), the alkene LXX is hydroxylated to glycol LXXI. For this purpose osmium tetroxide is a suitable reagent, for example in conjunction with N-methylmorpholine oxide hydrogenperoxide complex (see Fieser et al., "Reagents for Organic Synthesis," p. 690, John Wiley and Sons, Inc., New York (1967)). Thereafter, several methods are available for obtaining the formula-LXXII product. These are the same methods which are available for obtaining products XIII i Chart A above. In the preferred method, the glycol is converted to a bis(alkanesulfonic acid) ester and subsequently hydrolyzed to LXXII by methods known in the art (see, for example German Offenlegungsschrift No. 1,937,676, Derwent Farmdoc 6862R); see also U.S. Pat. No. 3,843,712. Another method is by way of a diformate by formolysis of the glycol (see U.S. Pat. No. 3,711,515).

Still another method is by way of a cyclic ortho ester. For this purpose, glycol LXXI is reacted with an ortho ester of the formula

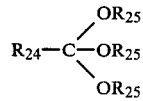

wherein $R_{24}$ is hydrogen, alkyl of one to 19 carbon atoms, inclusive, or aralkyl of 7 to 12 carbon atoms, inclusive, substituted with zero to 3 halo atoms; and $R_{25}$ is methyl or ethyl. There is then formed a cyclic ortho ester of the formula

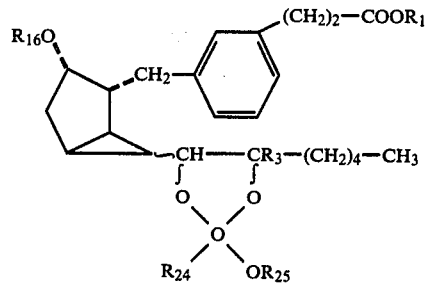

wherein $R_1$, $R_3$, $R_{16}$, $R_{24}$, $R_{25}$, and ∼ are as defined above. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethylorthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl)acetate.
Preferred are those ortho esters wherein $R_{24}$ is alkyl of one to 7 carbon atoms; especially preferred are those wherein $R_{24}$ is alkyl of one to 4.

Next, the cyclic orthoester LI is reacted with anhydrous formic acid to yield a diol diester of the formula

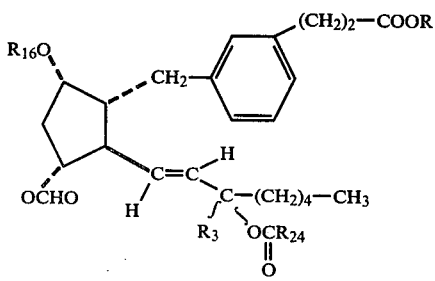

wherein $R_1$, $R_3$, $R_{16}$, $R_{24}$, and ∼ are as defined above.

By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid.

There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°-30° C. and is usually completed within about 10 minutes.

Finally, the diol diester LII is converted to product LXXII by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the nature of $R_{24}$ and the base proceeding in the case of alkali carbonates in a few minutes when $R_{24}$ is hydrogen but taking up to several hours when $R_{24}$ is ethyl, for example.

When the solvolysis proceeds too long or when conditions are too severe, ester groups at $R_1$ may be removed. They are however, readily replaced by methods known in the art. For example, the alkyl, cycloalkyl, and aralkyl esters are prepared by interaction of the formula-LXXII acids with the appropriate diazohydrocarbon. For example, when diazomethane is used, the methyl esters are produced. Similar use of diazoethane, diazobutane, 1-diazo-2-ethyl-hexane, diazocyclohexane, and phenyldiazomethane, for example, gives the ethyl, butyl, 2-ethylhexyl, cyclohexyl, and benzyl esters, respective.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389-394 (1954).

An alternative method for esterification of the carboxyl moiety comprises transformation of the free acid to the corresponding silver salt, followed by interaction of that salt with an alkyl iodide. Example of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters are prepared by silylating the acid to protect the hydroxy groups, for example, replacing each —OH with —O—Si—(CH₃)₃. Doing that may also change —COOH to —COO—Si—(CH₃)₃. A brief treatment of the silylated compound with water will change —COO—Si—(CH₃)₃ back to —COOH. Procedures for this silylation are known in the art. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH₃)₃ are changed back to —OH by treatment with dilute acetic acid. Procedures for these transformations are known in the art.

The above methods for esterification are of course useful for preparing the various esters of this invention within the scope of $R_1$, when the acids have been prepared by methods disclosed herein or known in the art. The free acids are also obtained from esters by use of an esterase enzyme for example that disclosed in U.S. Pat. No. 3,761,356.

Reference to Chart F will show the steps leading from a formula-LXIV alkene, readily available from the formula-LXVIII alkene of Chart E, to the $PGF_{1\alpha}$-type products of formula LXXV.

Still another method of synthesis for the inter-m-phenylene prostaglandin $E_1$ analogs of this invention is provided herein, utilizing 2-methylene-cyclopentanone intermediates of the formula

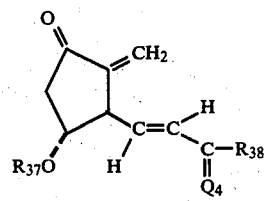
LXXXIX wherein $Q_4$ is

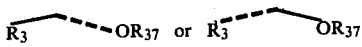

wherein $R_3$ is hydrogen or alkyl of one to 4 carbon atoms, inclusive, and wherein $R_{37}$ is tetrahydropyran-2-yl, tetrahydrofuranyl, 1-ethoxyethyl or a group of the formula

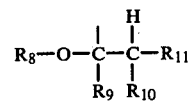

wherein $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —(CH₂)a— or —(CH₂)b—O—(CH₂)c— wherein a is 3, 4, or 5, b is one, 2, or 3, and c is one, 2, or 3 with the proviso that b plus c is 2, 3, or 4, and wherein $R_{11}$ is hydrogen or phenyl; and wherein $R_{38}$ is

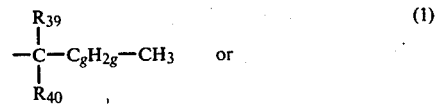
(1)

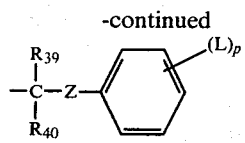

wherein $C_gH_{2g}$ is alkylene of one to 9 carbon atoms, inclusive, with one to 5 carbon atoms, inclusive, in the chain between —$CR_{39}R_{40}$— and terminal methyl, wherein $R_{39}$ and $R_{40}$ are hydrogen, alkyl of one to 4 carbon atoms, inclusive, or fluoro, being the same or different, with the proviso that one of $R_{39}$ and $R_{40}$ is fluoro only when the other is hydrogen or fluoro and the further proviso that neither $R_{39}$ nor $R_{40}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{39}R_{40}$— and the phenyl ring; and wherein L is alkyl of one to 4 carbon atoms, inclusive, fluoro, chloro, trifluoromethyl, or —$OR_{41}$— wherein $R_{41}$ is alkyl of one to 4 carbon atoms, inclusive, and p is zero, one, 2 or 3, with the proviso that not more than two L's are other than alkyl and when p is 2 or 3 the L's are either the same or different.

Reference to Chart H will make clear the steps by which intermediate LXXXIX is formed and converted to product XCIV. In Chart H, A is as defined above for Chart B, i.e. alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive; Q is

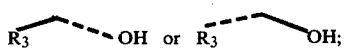

and $R_3$ and $R_{37}$ are as defined above.

The bicyclic lactone starting reactants of formula LXXXII are known in the art or are available by processes known in the art. For example, when $R_{38}$ is —$(CH_2)_4$—$CH_3$, and Q is

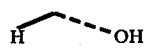

see Corey et al., J. Am. Chem. Soc. 92, 397 (1970). For other LXXXII lactones see, for example, U.S. Pat. Nos. 3,903,131, 3,962,293, 3,987,087, and British specification cited in Derwent Farmdoc No. 73279U.

CHART H

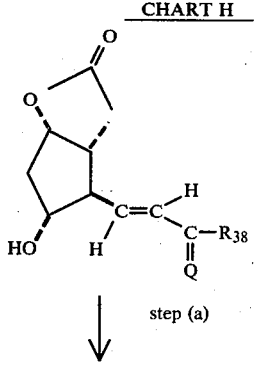

LXXXII

-continued

CHART H

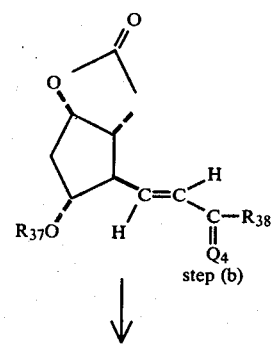

LXXXIII step (b)

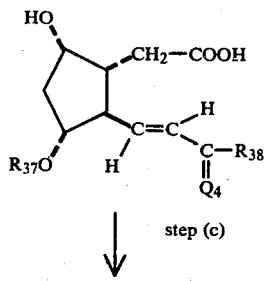

LXXXIV step (c)

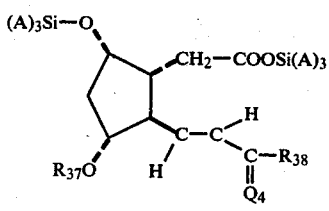

LXXXV step (d)

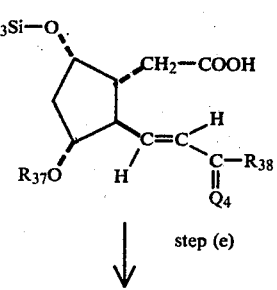

LXXXVI step (e)

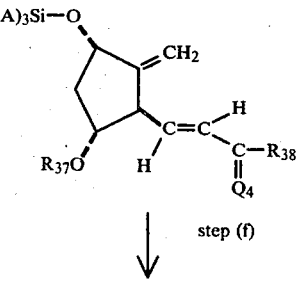

LXXXVII step (f)

-continued
CHART H

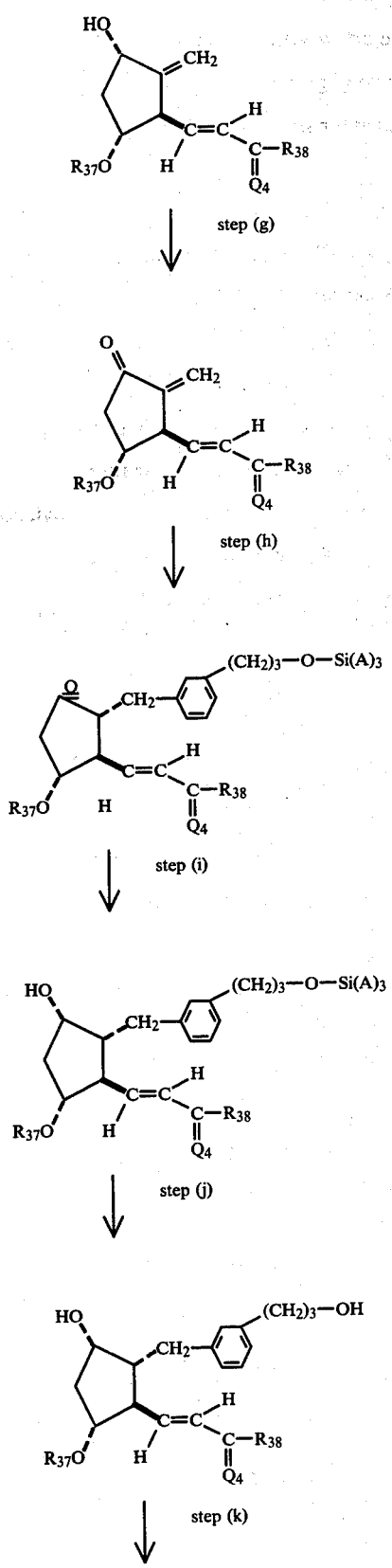

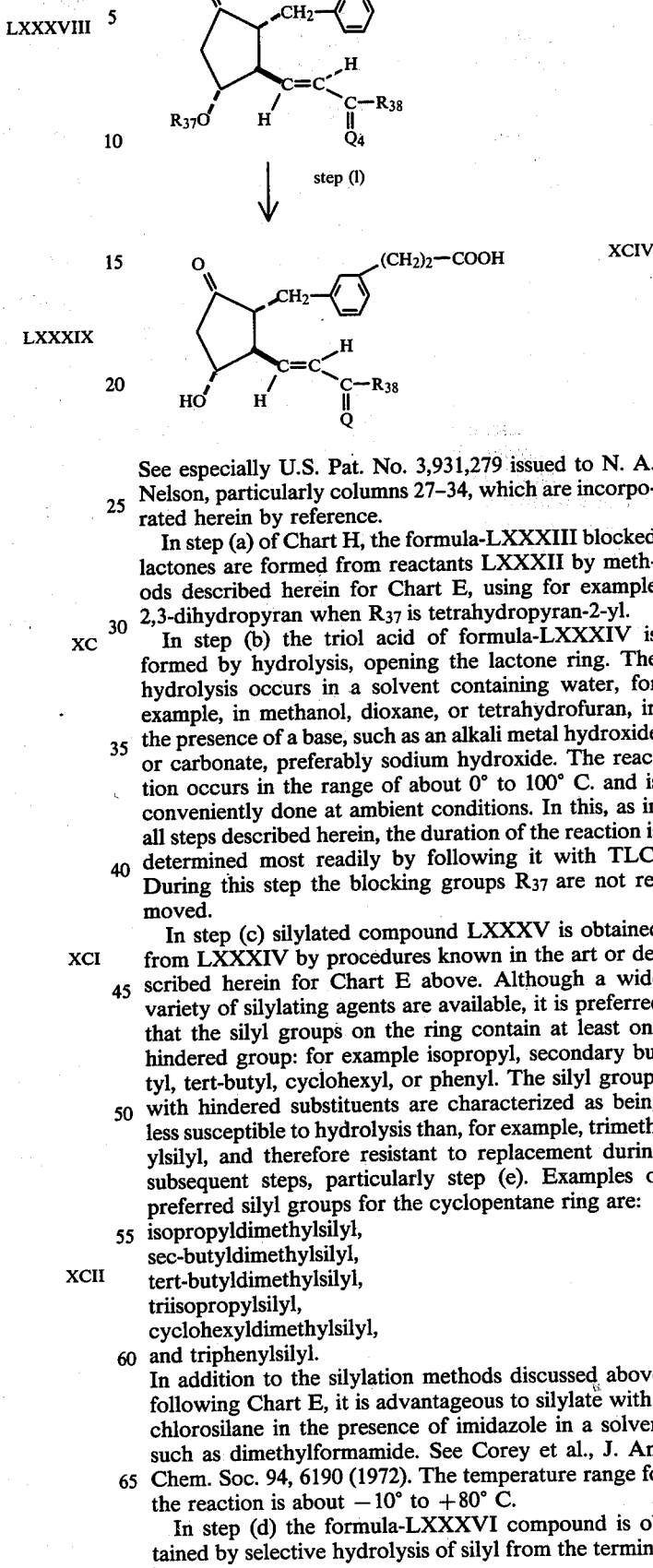

See especially U.S. Pat. No. 3,931,279 issued to N. A. Nelson, particularly columns 27–34, which are incorporated herein by reference.

In step (a) of Chart H, the formula-LXXXIII blocked lactones are formed from reactants LXXXII by methods described herein for Chart E, using for example 2,3-dihydropyran when $R_{37}$ is tetrahydropyran-2-yl.

In step (b) the triol acid of formula-LXXXIV is formed by hydrolysis, opening the lactone ring. The hydrolysis occurs in a solvent containing water, for example, in methanol, dioxane, or tetrahydrofuran, in the presence of a base, such as an alkali metal hydroxide or carbonate, preferably sodium hydroxide. The reaction occurs in the range of about 0° to 100° C. and is conveniently done at ambient conditions. In this, as in all steps described herein, the duration of the reaction is determined most readily by following it with TLC. During this step the blocking groups $R_{37}$ are not removed.

In step (c) silylated compound LXXXV is obtained from LXXXIV by procedures known in the art or described herein for Chart E above. Although a wide variety of silylating agents are available, it is preferred that the silyl groups on the ring contain at least one hindered group: for example isopropyl, secondary butyl, tert-butyl, cyclohexyl, or phenyl. The silyl groups with hindered substituents are characterized as being less susceptible to hydrolysis than, for example, trimethylsilyl, and therefore resistant to replacement during subsequent steps, particularly step (e). Examples of preferred silyl groups for the cyclopentane ring are:
isopropyldimethylsilyl,
sec-butyldimethylsilyl,
tert-butyldimethylsilyl,
triisopropylsilyl,
cyclohexyldimethylsilyl,
and triphenylsilyl.

In addition to the silylation methods discussed above, following Chart E, it is advantageous to silylate with a chlorosilane in the presence of imidazole in a solvent such as dimethylformamide. See Corey et al., J. Am. Chem. Soc. 94, 6190 (1972). The temperature range for the reaction is about −10° to +80° C.

In step (d) the formula-LXXXVI compound is obtained by selective hydrolysis of silyl from the terminal carboxyl group. Generally an alkali metal carbonate is employed in water and a cosolvent such as methanol, tetrahydrofuran or dioxane, in a temperature range of about −10° to +100° C. If the silyl group on the ring is hindered, a stronger base such as sodium hydroxide may be used to selectively remove the silyl group from the carboxyl.

In step (e), oxidative decarboxylation is employed to yield the formula-LXXXVII compound. See J. D. Bacha and J. K. Kochi, Tetrahedron, 24, 2215 (1968). Compound LXXXVI is treated in solution, for example in benzene, toluene, xylene, or heptane, with a copper (II) salt such as the acetate, chloride, or nitrate, solubilized with a compound such as pyridine, followed by a lead (IV) salt such as the acetate or benzoate. Decarboxylation may be done either thermally (60°–100° C.) or photochemically using radiation of about 3000–3700 Å as from mercury vapor lamps, in a temperature range of about 0° to 60° C.

In step (f), the compound of formula LXXXVIII is obtained by selective hydrolysis of the silyl groups without removing the $R_{37}$ blocking groups. For this purpose a base is used in a liquid medium such as dioxane or tetrahydrofuran. For unhindered silyl groups an alkali metal carbonate is useful; for hindered groups, such as tert-butyldimethylsilyl, a tetra-n-alkylammonium fluoride such as tetra-n-butylammonium fluoride is preferred, in a temperature range of −10° to +50° C.

In step (g) the formula-LXXXIX ketone is obtained by oxidation. Useful for this purpose is pyridinium chlorochromate, Collins reagent, and especially Jones reagent at about −40° C. to about 25° C.

In step (h) compound XC is obtained by conjugative addition with a cuprate reactant prepared from

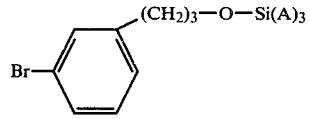

wherein $Si(A)_3$ is as defined above. For the synthesis of the cuprate reagent see, for example, Posner, Org. React. 19, 1 (1972) and Normant, Synthesis 63 (1972). See also Posner for typical conditions for addition to an enone. It is conveniently done in a solvent such as diethyl ether or tetrahydrofuran at about −78° to 0° C.

In step (i) compound XCI is obtained by reduction of the ketone, using methods known in the art, for example sodium borohydride at about 0° C.

In step (j) the terminal silyl group is removed to form compound XCII, using methods described above, for example hydrolysis with tetra-n-butylammonium fluoride for tert-butyldimethylsilyl groups.

In step (k) compound XCIII is obtained by oxidation, using for example Jones reagent.

Finally, in step (l) of Chart H the $R_{37}$ blocking groups are removed by mild acid hydrolysis as known in the art, yielding final acid compound XCIV.

When an ester within the scope of compound VI is desired, it is obtained from the formula-XCIV acid by methods known in the art and described herein. For example the acid may be treated with diazomethane to yield the methyl ester.

Another route to the esters is shown in Chart I wherein Q, $Q_4$, $R_{37}$, and $R_{38}$ are as defined above and $R_2$ is an ester group within the scope of $R_1$. Accordingly, compound XCIII from step (k) of Chart H is esterified at the C-1 carboxyl position by methods known in the art to yield compound XCV. Thereafter the $R_{37}$ blocking groups are removed following the procedures used for step (l) of Chart H, as known in the art.

Chart J shows an alternate route of synthesis of the of the formula-LXXXVIII methylene compound starting with the formula-LXXXIII lactone of Chart H. In Chart J the terms $Q_4$, $R_{37}$, and $R_{38}$ have the same meaning as in Chart H; $R_{17}$ represents (1) carboxyacyl $R_{13}$ as defined for Chart E above and including, for example, formyl, acetyl, ivalcyl, and the like, or (2) an aromatic acyl group such as benzoyl or substituted benzoyl, nonesterified phthaloyl, naphthoyl, or substituted naphthoyl as exemplified above for Chart E.

CHART I

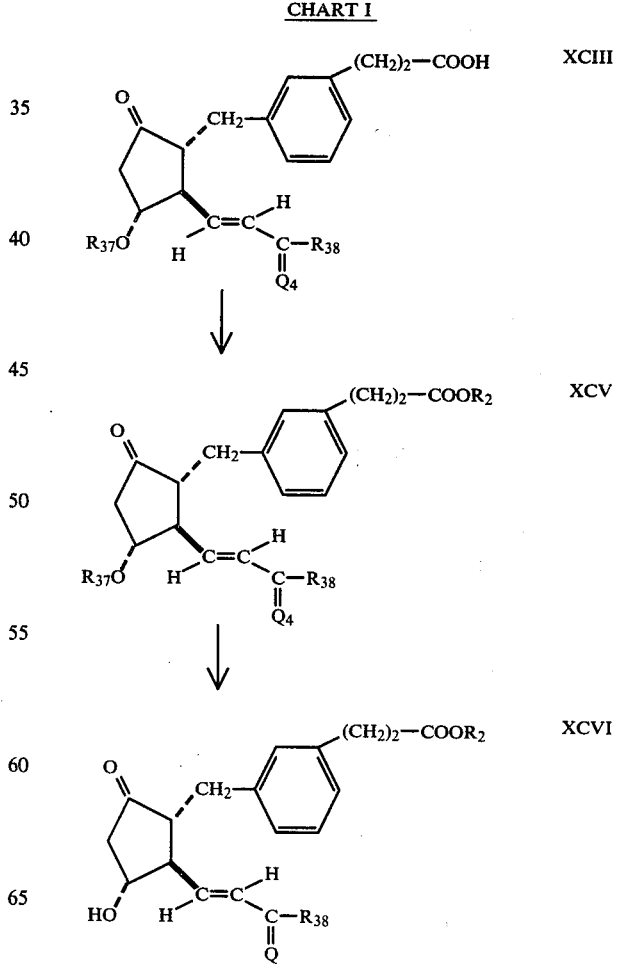

CHART J

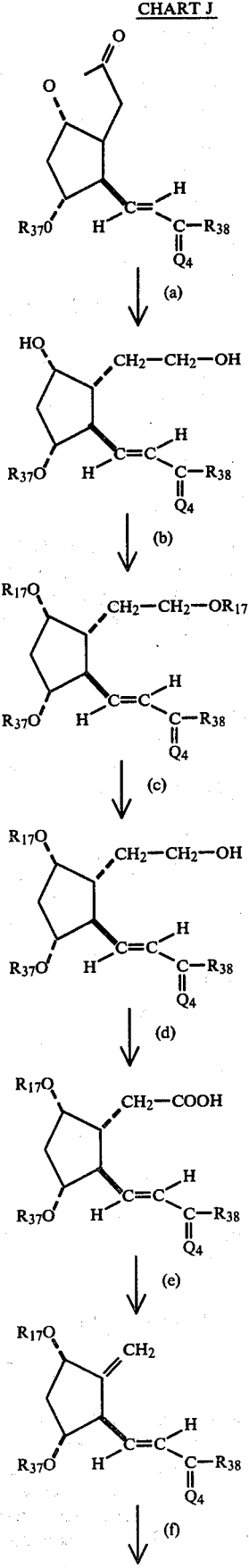

LXXXIII

XCVII

XCVIII

XCIX

C

CI

-continued
CHART J

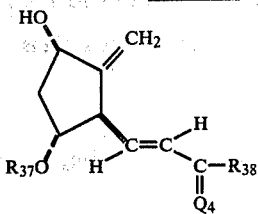

LXXXVIII

In step (a) reduction of the formula-LXXXIII lactone yields the formula-XCVII diol. For this reduction, lithium aluminum hydride or diisobutylaluminum hydride are useful at 0°–35° C. Especially preferred is sodium bis(2-methoxyethoxy)aluminum hydride.

In step (b) the formula-XCVIII diacylated compound is formed by acylation using methods known in the art or described herein for Chart E. The two $R_{17}$ groups may be the same or different, for example one may be acetyl and the other pivaloyl. For the purpose herein it is preferred that the acyl group on the ring be somewhat more resistant to replacement by hydrolysis than the acyl group at the terminal position on the chain and one such preferred combination is with pivaloyl on the ring and acetyl on the chain.

In step (c) the monoacylated compound of formula XCIX is obtained by selective hydrolysis. Generally a mild base such as potassium carbonate in methanol is sufficient to deacylate the terminal group on the chain. The hydrolysis of such esters is well known in the art and a wide choice of reagents and conditions is available to one skilled in the art.

In step (d) the formula-C acid is formed by oxidation, employing for example, the Jones reagent (J. Chem. Soc. 39, (1946)) at −40° to 25° C. in acetone.

In step (e) the formula-CI compound is obtained by oxidative decarboxylation, as described for Chart H above, using for example lead tetraacetate.

Finally in step (f) of Chart J the formula-LXXXVIII methylene compound is obtained on base hydrolysis of the monoacylated compound CI. Where $R_{17}$ is a hindered ester stronger bases or more rigorous treatment are used than for step (c), for example with potassium carbonate at 50°–100° C. or with sodium or potassium hydroxide.

Chart K shows an alternate method for preparing the inter-m-phenylene-PGF$_{1\alpha}$ compounds of this invention. The formula-XCI starting materials have been described above as produced by step (i) of Chart H. In Chart K, the terms A, $Q_4$, $R_{17}$, $R_{37}$, and $R_{38}$ are as defined for Chart J above.

In step (a) the formula-XCI compound is acylated at the free hydroxyl at C-9, using methods described herein or known in the art.

In step (b) the formula-CIII compound is obtained by preferential hydrolysis to remove the silyl groups. Thereafter, in step (c) the terminal C-1 hydroxyl groups are oxidized to carboxyl groups using methods described above for step (k) of Chart H or methods known in the art.

In step (d) the C-9 acyl blocking groups $R_{17}$ are removed, as by base hydrolyses following the methods described above for step (f) of Chart J. Finally in step (e) the C-11 and C-15 blocking groups $R_{37}$ are removed by mild acid hydrolysis as known in the art, to yield the formula-CVI products.

For preparing 15-alkyl products of formula-CVI when the starting material XCI of Chart K has no 15-alkyl substitution at C-15, i.e. wherein $Q_4$ is

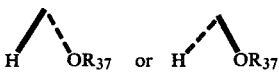

a process for C-15 alkylation is available, relying on analogous chemistry disclosed above for Chart C.

CHART K

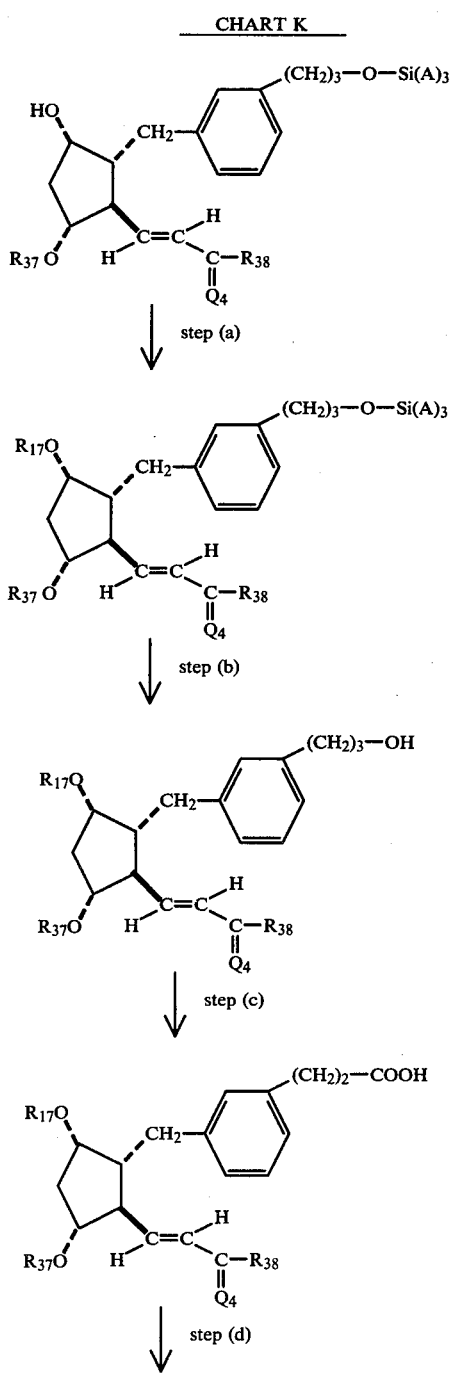

-continued
CHART K

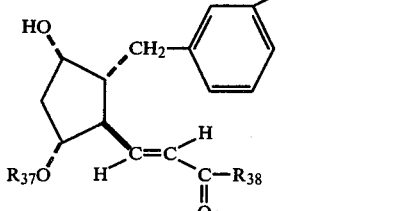 CV step (e)

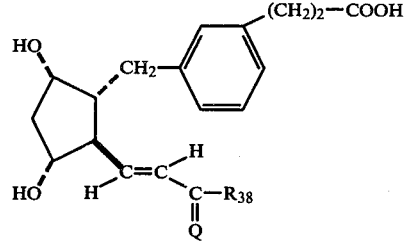 CVI

Furthermore, interconversions of the PGE and PGF type analogs shown in Charts B and D where the terminal group is n-pentyl are likewise applicable to the other alkyl-, phenoxy-, and phenyl-terminated type analogs within the scope of formulas VI and VII wherein $R_{38}$ is other than n-pentyl.

Likewise, the preparation of PGA-type analogs of formula VIII wherein $R_{38}$ is other than n-pentyl is accomplished by analogous methods to those shown in Chart D and discussed in connection therewith.

Still another process for preparing the PGF-type analogs of this invention where the terminal group $R_{38}$ is other than n-pentyl is by starting with 4,5,6-trinor-3,7-inter-m-phenylene-PGF$_{1\alpha}$, converting to an aldehyde of the formula

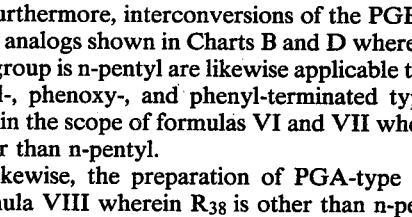

wherein $R_1$ is as defined above, by ozonolysis using methods known in the art (see for example Fieser and Fieser, Reagents for Organic Synthesis, Vol. 1, pp. 773-777, John Wiley, 1967), followed by a Wittig synthesis using for example an ylid derived from

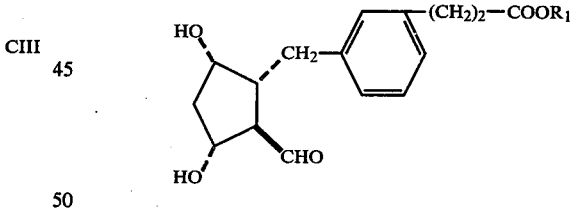

and finally reducing the $C_{15}$ carbonyl by methods known in the art.

The novel intermediates of Charts A, B, C, D, E, F, H, I, J, and K including those compounds represented by formulas VI, IX–XII, XIV–XVIII, LXIII–LXXI, LXXIV, LXXXIII–XCIII, XCV, and XCVII–CVI are frequently not isolated but used directly for a subsequent process step. When they are isolated, they are purified by methods known in the art, for example partition extraction, fractional crystallization, and, preferably, silica gel column chromatography.

The products represented by formulas VII, XIII, LXXII, and LXXV obtained from these intermediates are often a mixture of 15-α and 15-β isomers. These are separated by methods known in the art, for example, by chromatography on neutral silica gel. In some instances, particularly where $R_3$ is alkyl, the lower alkyl esters are more readily separated than are the corresponding acids. In those cases wherein $R_1$ is hydrogen, it is advantageous to esterify the mixture of acids, as with diazomethane to form the methyl esters, separate the two epimers, and then, if desired, replace the carboxyl methyl with hydrogen by methods known in the art.

When an optically active intermediate or starting material is employed, subsequent steps yield optically active intermediates or products. That optical isomer of bicyclo hexene XXX is used which will yield product LXXII, for example, in the configuration corresponding to that of the naturally occurring prostaglandins. When the racemic form of the intermediate or starting material is employed, the subsequent intermediates or products are obtained in their racemic form.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 infrared spectrophotometer. Except when specified otherwise, undiluted (neat) samples are used.

NMR spectra are recorded on a Varian A-60, A-60D, or T-60 spectrophotometer using deuterochloroform solutions with tetramethylsilane as an internal standard (downfield).

Mass spectra are recorded on a CEC Model 110B Double Focusing High Resolution Mass Spectrometer or an LKB Model 9000 Gas Chromatograph-Mass Spectrometer (ionization voltage 70 ev.).

Circular dichroism curves are recorded on a Carey 60 recording spectropolarimeter.

Specific rotations are determined for solutions of a compound in the specified solvent with a Perkin-Elmer Model 141 Automatic Polarimeter.

"Brine", herein, refers to an aqueous saturated sodium chloride solution.

"Skellysolve-B" refers to mixed isomeric hexanes.

Silica gel chromatography, as used herein is understood to include elution, collection of fractions, and combination of those fractions shown by TLC (thin layer chromatography) to contain the desired product free of starting material and impurities.

"Concentrating", as used herein, refers to concentration under reduced pressure, preferably at less than 50 mm. and at temperatures below 35° C.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Preparation 1 m-(Bromomethyl)benzylmalonate, Diethyl Ester (Formula XXII)

A solution of diethyl malonate (30.3 g.) in 600 ml. of tetrahydrofuran is treated with potassium tertiary butoxide (10.52 g.) for 5 min. at about 25° C. Thereupon α,α'-dibromo-m-xylene (25.0 g.) is added and the mixture stirred at ambient temperature for 2.5 hr. The reaction is quenched by addition of 100 ml. of water and 50 ml. of 5% hydrochloric acid. The mixture is extracted with diethyl ether and the organic phase is dried over sodium sulfate and concentrated to an oil. The crude product, 45.3 g., is subjected to silica gel chromatography, eluting with Skellysolve B and then Skellysolve B-ethyl acetate (90:10). Yield of title compound: 20.2 g., having NMR spectral peaks at 7.17, 4.40, 4.34-3.96, and 1.38-1.06δ.

Preparation 2

3-(m-Bromomethyl)phenylpropionate, Methyl Ester (Formula XXIII)

The formula-XXII m-(bromomethyl)benzyl-malonate, diethyl ester (Preparation 1, 20.9 g.) is treated with 20 ml. of 48% hydrobromic acid on a steam bath for 20 hr. The reaction mixture is diluted with 200 ml. of water and extracted with diethyl ether. The organic phase is washed with water, dried over sodium sulfate, and concentrated to an oil, now the diacid.

The product above, in 200 ml. of xylene, is heated at reflux for 2.5 hr., until evolution of carbon dioxide is finished, and the mixture is concentrated. The residue is converted to the title compound by reaction with diazomethane in ether solution, followed by washing with ice-cold dilute sodium bicarbonate solution, drying, and concentrating to yield crude product.

The product of several preparations, 45 g., is subjected to silica gel chromatography, eluting with 7.5–10% ethyl acetate in Skellysolve B to obtain the title compound, 15.2 g., having NMR spectral peaks at 7.20, 4.47, and 3.66δ.

EXAMPLE 1 dl-6-Endo-(1-heptenyl)-2-exo-{m-[2-(methoxycarbonylethyl]}benzyl-bicyclo[3.1.0]hexan-3-one
(Formula X, wherein $R_{30}$ is methyl and ∼ is endo).

Refer to Chart A. A solution of the formula-XXIII 3-(m-bromomethyl)phenyl propionate, methyl ester (Preparation 2, 14.82 g.) in 280 ml. of tetrahydrofuran is treated with a mixture of 6-endo(1-heptenyl)-bicyclo[3.1.0]hexan-3-one (11.0 g.) and potassium t-butoxide (7.0 g.) in 560 ml. of tetrahydrofuran at about 25° C. for 45 min. The reaction is quenched by addition of 100 ml. of water and 75 ml. of 5% hydrochloric acid. About 3 ml. of pyridine is added and the mixture is concentrated under reduced pressure. The residue is extracted with ether, then washed with water and brine, dried over sodium sulfate, and concentrated. The crude product is subjected to silica gel chromatography, eluting with 10% ethyl acetate in Skellysolve B, to yield the title compound, 7.15 g., having NMR spectral peaks at 7.20, 7.12, 7.05, 5.84-5.40, 5.10-4.68, and 3.64δ; and mass spectral peaks at 368, 350, 337, 326, and 319.

EXAMPLE 2 dl-6-Endo-(1,2-dihydroxyheptyl)-2-exo-{m-[2-(methoxycarbonyl)ethyl]}benzyl-bicyclo[3.1.0]hexan-3-one. (Formula XI, wherein $R_{30}$ is methyl and ∼ indicates attachment to the cyclopropane ring in endo configuration).

Refer to Chart A. A solution of the formula-X 6-endo(1-heptenyl)-2-exo-{m-[2-(methoxycarbonyl)ethyl]}-benzyl-bicyclo[3.1.0]hexan-3-one (Example 1, 7.0 g.) in 190 ml. of tetrahydrofuran is treated at 45°-50° C. for 90 min. with a solution of potassium chlorate (6.3 g.) and osmium tetroxide (0.36 g.) in 75 ml. of water. Thereupon most of the solvent is removed under reduced pressure and the residue extracted with dichloromethane. The organic phase is washed with water and brine, dried over sodium sulfate, and concentrated. The crude product, 8.1 g., is taken up in a mixture of ethyl acetate and cyclohexane (1:1) and subjected to silica gel chromatography to yield the title compound as the mixed erythro and threo glycols 4.03 g., having NMR peaks at 7.12, 7.05, 4.32-4.14, and 3.80δ; and having mass spectral peaks at 384, 366, and 335.

EXAMPLE 3 dl-4,5,6-Trinor-3,7-inter-m-phenylene-PGE$_1$, Methyl Ester (corresponding to VI$_\alpha$, wherein Q is

and $R_1$ is methyl), and dl-4,5,6-Trinor-3,7-inter-m-phenylene-15-epi-PGE$_1$, Methyl Ester (corresponding to formula VI$_\beta$, wherein Q is

and $R_1$ is methyl).

Refer to Chart A. A solution of the formula-XI glycols, i.e. 6-endo-(1,2-dihydroxyheptyl)-2-exo-{m-[2-(methoxycarbonyl)ethyl]}benzyl-bicyclo[3.1.0]hexan-3-one (Example 2, 4.0 g.) in 60 ml. of pyridine is cooled to 10° C. and treated with 6 ml. of methanesulfonyl chloride added dropwise. The reaction mixture is stirred for 2.5 hr. at 0° C., then cooled to −10° and quenched with water below 0° C. A mixture of 150 ml. of ice and water is added and the whole is extracted with dichloromethane. The organic phase is washed with ice-cold dilute hydrochloric acid, water, and cold dilute aqueous sodium bicarbonate, dried over sodium sulfate, and concentrated to a viscous oil.

The formula-XII bismesylate above is solvolyzed in 300 ml. of acetone and 100 ml. of water at about 25° C. for about 16 hr. The low boiling solvent is removed under reduced pressure and the residue extracted with dichloromethane. The organic phase is washed with cold dilute sodium bicarbonate solution, dried over sodium sulfate, and concentrated. The residue, 4.7 g. is taken up in 100 ml. of ethyl acetate-cyclohexane (1:1) and subjected to silica gel chromatography, eluting with 0-10% methanol in ethyl acetate. The two title compounds are obtained separately, the less polar formula-VI$_\beta$ 15-epi isomer, 325 mg., and the formula-VI$_\alpha$ product, 385 mg. The latter has NMR spectral peaks at 7.28-6.85, 5.55-5.35, 4.08-3.86, 3.63, 1.33, and 0.90 δ and mass spectral peaks at 384 and 366. The 15-epi compound is distinguishable by the shift in the NMR spectra for the vinyl proton region of 5.60-5.42 δ compared with 5.55-5.35 δ for the formula-VI$_\alpha$ product.

EXAMPLE 4 dl-4,5,6-Trinor-3,7-inter-m-phenylene-PGF$_{1\alpha}$, Methyl Ester (corresponding to formula VII, wherein Q is

and $R_1$ is methyl).

Refer to Chart B. A solution of the formula-VI$_\alpha$ PGE$_1$-type compound, i.e. dl-4,5,6-trinor-3,7-inter-m-phenylene-PGE$_1$, methyl ester (Example 3, 140 mg.) in 20 ml. of tetrahydrofuran is treated with 2.5 ml. of hexamethyldisilazane and 0.25 ml. of trimethylchlorosilane at about 25° C. for 16 hr. The mixture is concentrated under reduced pressure and the residue taken up in 75 ml. of methanol. The resulting solution is cooled to −5° C. and treated with a solution of sodium borohydride (0.3 g.) in 20 ml. of ice-cold methanol at about 0° C. for 30 min. The reaction mixture is quenched with 10 ml. of acetone, acidified with dilute acetic acid, and stirred at about 25° C. for one hr. The mixture is diluted with water and extracted with ethyl acetate. The organic phase is washed with cold dilute sodium bicarbonate solution, dried, and concentrated. The residue, 120 mg., is subjected to silica gel chromatography, eluting with 0-10% methanol in ethyl acetate, to yield the title compound, 90 mg., m.p. 63°-64° C., having NMR peaks at 7.23-6.9, 5.62-5.4, 4.06-3.85, 3.63, 3.15, 1.35, and 0.90 δ; and having mass spectral peaks at 386, 368, and 314.

EXAMPLE 5 dl-4,5,6-Trinor-3,7-inter-m-phenylene-PGA$_1$, Methyl Ester (corresponding to formula VIII wherein Q is

and $R_1$ is methyl).

Refer to Chart D. A solution of the formula-VI$_\alpha$ PGE$_1$-type compound, i.e. dl-4,5,6-trinor-3,7-inter-m-phenylene-PGE$_1$, methyl ester (Example 3, 200 mg.) in 10 ml. of dichloromethane and 0.4 ml. of pyridine is cooled to 3° C. and treated with 0.34 ml. of trifluoroacetic anhydride for 20 min. The resulting bis-trifluoroacetate is treated with 0.68 ml. of triethylamine at 0° to 5° C. for 2.5 hr., then with 8 ml. of methanol at about 25° C. for 1.5 hr. The mixture is concentrated and the residue taken up in diethyl ether. The organic phase is washed with brine, cold dilute potassium bisulfate solution, brine, cold 0.2 N potassium bicarbonate solution, and brine, dried over magnesium sulfate, and concentrated. The residue, 300 mg., is subjected to silica gel chromatography eluting with 30-50% ethyl acetate in hexane to obtain the title compound, 181 mg., having NMR peaks at 7.53-7.37, 7.18-6.98, 6.20-6.07, 5.33-5.23, 3.62, and 0.86 δ: and mass spectral lines at 441, 425, 409, 385, 366, and 335.

Preparation 3

Optically Active Bicyclo[3.1.0]hex-2-ene-6-endo-carboxaldehyde

Following the procedure of Preparation 1 of U.S. Pat. No. 3,711,515, racemic bicyclo[3.1.0]hex-2-ene-6-endo-caroxaldehyde is prepared from bicyclo[2.2.1-]hepta-2,5-diene and peracetic acid.

The racemic compound is resolved by the procedure of Example 13 of U.S. Pat. No. 3,711,515, forming an oxazolidine as follows.

Racemic bicyclo[3.1.0]hex-2ene-6-endo-carboxaldehyde (12.3 g.) and 1-ephedrine (16.5 g.) are dissolved in about 150 ml. of benzene. The benzene is removed under vacuum and the residue is taken up in about 150 ml. of isopropyl ether. The solution is filtered, then cooled to −13° C. to yield crystals of 2-endo-bicyclo[3.1.0]hex-2-en-6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2.2 g. m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatography-grade (Merck), 0.05–0.2 mm. particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular curve are ($\lambda$ in nm., $\theta$): 350, 0; 322.5, −4,854; 313, −5,683; 302.5, −4,854; 269, 0; 250, 2,368, 240, 0; and 210; −34,600.

Preparation 4 m-(Bromomethyl)-benzylmalonate, Dimethyl Ester (Formula LXXVII)

Refer to Chart G. A solution of dimethyl malonate (26.42 g.) in 600 ml. of tetrahydrofuran is treated with potassium tertiary butoxide (10.52 g.) for 5 min. at about 25° C. Thereupon $\alpha,\alpha'$-dibromo-m-xylene (25.0 g.) is added and the mixture stirred at ambient temperature for 2.5 hr. The reaction is quenched by addition of 100 ml. of water and 50 ml. of 5% hydrochloric acid. The mixture is extracted with diethyl ether and the extract is washed with water and brine, dried over magnesium sulfate and concentrated to an oil. The crude product is subjected to chromatography on silica gel, eluting with Skellysolve B-ethyl acetate (first 95:5 and then 50:50). Yield of title compound: 31.5 g., having NMR peaks at 3.67, 4.43, and 7.20 $\delta$.

Preparation 5 m-(Acetoxymethyl)-benzylmalonate, Dimethyl Ester (Formula LXXVIII)

Refer to Chart G. A mixture of m-(bromomethyl)-benzylmalonate, dimethyl ester (Preparation 2, 31.5 g.) and potassium acetate (17.5 g.) in 280 ml. of dimethylformamide is heated at 50° C. for about 0.5 hr. until no starting material is shown by TLC (thin layer chromatography) on silica gel plates, in Skellysolve B-ethyl acetate (75:25). The mixture is taken up in diethyl ether-Skellysolve B (1:1) and washed with water and brine, dried over magnesium sulfate, and concentrated to an oil. The crude product is subject to silica gel chromatography, eluting with Skellysolve B-ethyl acetate (90:10 to 30:70). Yield of title compound: 9.66 g., having infrared absorption at 1740, 1610, 1595, 1490, 1435, 1230, 1155, and 1030 cm$^{-1}$; NMR peaks at 2.08, 3.67, 5.07, and 7.19 $\delta$; and mass spectral peaks at 294, 134, 101, 74, 59, 45, 43, 42, 29, and 15.

Preparation 6 m-(Hydroxymethyl)-phenylpropionic Acid (Formula LXXIX)

Refer to Chart G. A solution of m-(acetoxymethyl)-benzylmalonate, dimethyl ester (Preparation 3, 9.16 g.) in 45 ml. of dioxane is treated with 137 ml. of 10% sodium hydroxide at about 25° C. for 15 min. The mixture is acidified to pH 1.0 with sulfuric acid, treated with an additional 3 ml. of sulfuric acid, and heated at reflux for about 36 hr. The mixture is cooled, diluted with 430 ml. brine and extracted with chloroform. The extract is washed with brine, dried over magnesium sulfate, and concentrated. Yield of title compound: 4.31 g., having NMR peaks at 2.40–3.18, 4.58, 7.17, and 7.53 $\delta$.

Preparation 7 m-(Hydroxymethyl)-phenylpropionate, Methyl Ester (Formula LXXX, wherein $R_{19}$ is methyl)

Refer to Chart G. A solution of m-(hydroxymethyl)-phenylpropionic acid (Preparation 4, 4.31 g.) in 7.15 ml. of dichloromethane is treated with 2.29 g. of methanol and 0.076 ml. of concentrated sulfuric acid, heated at reflux for 3.0 hr. The mixture is cooled, diluted with brine, and extracted with diethyl ether. The extract is washed with sodium bicarbonate solution and brine, dried over magnesium sulfate, and concentrated to an oil. Yield of title compound: 3.31 g. On subjecting the product to silica gel chromatography, eluting with Skellysolve B-ethyl acetate (75:25 to 35:65), there is recovered 95% of the product in selected fractions, having NMR peaks at 2.37–3.17, 3.60, 4.58, and 7.15 $\delta$.

Preparation 8

(m-Formylphenyl)propionate, Methyl Ester (Formula LXXXI, wherein $R_{19}$ is methyl)

Refer to Chart G. A mixture of m-(hydroxymethyl)-phenylpropionate, methyl ester (Preparation 5, 3.72 g.) and 40.92 ml. of 1 M. ceric ammonium nitrate solution in 40.92 ml. of acetic acid is stirred at 65° C. for 2 hr. Then another 2 ml. of ceric ammonium nitrate solution is added and treatment continued at 65° C. for one hr. The mixture is cooled, diluted with brine and extracted with diethyl ether. The ether extract is washed with brine and water, dried over sodium sulfate, and concentrated to an oil.

The above product, containing the acid, is converted to the title compound with diazomethane. The mixture is quenched with 10% acetic acid, diluted with brine, and extracted with diethyl ether. The ether extract is washed with sodium bicarbonate solution and brine, dried, and concentrated to the title compound, 2.90 g. Taking additional material, the combined lot (4.48 g.) is subjected to silica gel chromatography, eluting with Skellysolve B-ethyl acetate (90:10 to 60:40) to yield 3.532 g., b.p. 0.35 mm. 105°–107° C. and having NMR peaks at 2.50–3.28, 3.65, 7.17–7.93, and 10.00 $\delta$: mass spectral peaks at 192, 161, 133, 132, 131, 119, 105, 103, 77 and 51; and infrared absorption bands at 3000, 2940. 2840, 2720, 1735, 1700, 1605, 1585, 1485, 1435, 1295, 1240, 1200, 1160, 1145, 795, 690, and 650 cm$^{-1}$; and $R_f$ 0.36 (TLC on silica gel in 25% ethyl acetate-Skellysolve B).

EXAMPLE 6

1-Bicyclo[3.1.0]hex-2-ene-6-endo-carboxaldehyde Neopentyl Glycol Acetal (Formula XXX: $R_5$ and $R_6$ taken together are —$CH_2$—$C(CH_3)_2$—$CH_2$— and ∼ is endo).

A mixture of 2,2-dimethyl-1,3-propanediol (900 g.), 5 l. of benzene and 3 ml. of 85% phosphoric acid is heated at reflux. To it is added, in 1.5 hr., a solution of optically active bicyclo[3.1.0]hex-2-ene-6-endo-carboxaldehyde (Prep. 3, 500 g.) in one liter of benzene. Provison is made to take off azeotropically distilled water with a Dean-Strak trap. After 3 hr. the mixture is cooled and extracted with 2 liters of 5% sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to $-13°$ C. to yield 300 g. of the title compound, m.p. 52°–55° C., and having NMR peaks at 0.66 1.20, 0.83–2.65, 3.17–3.8, 3.96, and 5.47–5.88 $\delta$, $[\alpha]_D-277°$ (C=0.8976 in methanol), and $R_f$0.60 (TLC on silica gel in 25% ethyl acetate in mixed isomeric hexanes). Further work-up of the mother liquors yields 50–100 g. of additional product.

Following the procedures of Example 6 but replacing the aldehyde with optically active bicyclo[3.1.0]hex-2-ene-6-exo-carboxaldehyde (see U.S. Pat. No. 3,711,515), there is obtained the corresponding formula-XXX acetal.

Following the procedures of Example 6 but using either the endo or exo form of the aldehyde and substituting for 2,2-dimethyl-1,3-propanediol one of the following glycols: ethylene glycol, 1,2-propanediol, 1,2-hexanediol, 1,3-butanediol, 2,3-pentanediol, 2,4-hexanediol, 2,4-octanediol, 3,5-nonanediol, 3,3-dimethyl-2,4-heptanediol, 4-ethyl-4-methyl-3,5-heptanediol, phenyl-1,2-ethanediol and 1-pentyl-1,2-propanediol, there are obtained the corresponding formula-XXX acetals.

EXAMPLE 7 dl-{m-[2-(Methoxycarbonyhl)ethyhl]phenyl}-7-oxa-tricyclo[4.2.0.0$^{2,4}$]octane-6-endo-carboxaldehyde Neopentyl Glycol Acetal (Formula LXIII wherein $R_5$ and $R_6$ taken together are —$CH_2$—$C(CH_3)_2$—$CH_2$—, $R_{19}$ is methyl, and ∼ is endo).

Refer to Chart E, step (a). A solution of racemic bicyclo(3.1.0)hex-2-ene-6-endo-carboxaldehyde neopentyl glycol acetal (corresponding to the optically active formula-XXX compound of Example 6, 5.82 g.) and the formula-LXXXI (m-formylphenyl) propionate, methyl ester (Preparation 8, 0.96 g.) insufficient benzene to bring to a volume of 30 ml. is charged to a Pyrex photolysis vessel equipped with an immersible water-cooled cold-finger and fritted gas inlet tube. Dissolved oxygen is removed by bubbling nitrogen through the solution. The mixture is then irradiated at 350 nm. with a Rayonet Type RS Preparative Photo-chemical Reactor (The Southern New England Ultraviolet Co., Middletown, Conn.) equipped with six RUL 3500 A lamps. After 17 hr. the photolysate is concentrated under reduced pressure to an oil, which is subjected to silica gel chromatography. Elution with 10–75% ethyl acetate in Skellysolve B (mixture of isomeric hexanes) and finally ethyl acetate yields separate fractions of the recovered starting materials and the formula-LXIII title compound, an oil, 0.73 g., having NMR peaks at 0.67, 1.18, 3.65, 4.97–5.55, and 6.93–7.57 $\delta$; mass spectral peaks at 386, 385, 115, 108, 84, 79, 69, 59, 45, 43, 41, and 29; infrared absorption bands at 3020, 2940, 2860, 1735, 1605, 1590, 1470, 1435, 1395, 1360, 1290, 1230, 1195, 1160, 1110, 1060, 1020, 1005, 985, 930, 915, 835, 785 and 705 cm$^{-1}$; and $R_f$0.18 (TLC on silica gel in ethyl acetate-Skellysolve B(25:75)).

EXAMPLE 8 dl-2-Exo-{m[2-(methoxycarbonyl)ethyl]benzyl}-3-exo-(pivaloyloxy)-bicyclo[3.1.0]hexane-6-endo-carboxaldehyde Neopentyl Glycol Acetal (Formula LXV wherein $R_5$ and $R_6$ taken together are —$CH_2$—$C(CH_3)_2$—$CH_2$—, $R_{18}$ is pivaloyl, $R_{19}$ is methyl, and ∼ is endo).

(I). Refer to Chart E, steps (b) and (c). A mixture of the formula-LXIII oxetane (Example 7, 0.36 g., previously stirred with Raney Nickel catalyst and filtered), 10 ml. of ethyl acetate, 5 ml. of ethanol, and 0.25 g. of 10% palladium on charcoal is subjected to hydrogenation at one atmosphere at 25° C. until one molar equivalent has been absorbed. The mixture is filtered and concentrated to the formula LXVI compound, a colorless oil having $R_f$0.29 (TLC on silica gel plate in ethyl acetate-Skellysolve B (50:50)).

(II). The product of part (I) is dissolved in 10 ml. of pyridine and treated with 0.35 ml. of pivaloyl chloride for 2 days at about 25° C. The reaction mixture is mixed with 100 ml. of water, 200 ml. of diethyl ether, and saturated aqueous copper (II) sulfate. The ether extract is washed with water, saturated aqueous sodium bicarbonate, and brine, and dried over magnesium sulfate. Concentration under reduced pressure yields an oil, 0.56 g., which after silica gel chromatography (eluting with first dichloromethane and then ethyl acetate-Skellysolve B (35:65)) yields the title compound as an oil, 0.48 g., having $R_f$0.42 (TLC on silica gel in ethyl acetate-Skellysolve B (25:75)); NMR peaks at 0.72, 1.21, 3.65, 4.18 (doublet, J=6.5 Hz), 5.00, and 6.80-7.40 $\delta$.

EXAMPLE 9 dl-2-Exo-{m-[2-(methoxycarbonyl)ethyl]benzyl}-3-exo-(pivaloyloxy)bicyclo[3.1.0]hexane-6-endo-carboxaldehyde (Formula LXVII, wherein $R_{16}$ is pivaloyl, $R_{20}$ is methyl, and ∼ is endo).

Refer to Chart E, step (d). The formula-LXV acetal, i.e. dl-2-exo-{m-[2-(methoxycarbonyl)ethyl]benzyl}-3-exo(pivaloyloxy)bicyclo[3.1.0]hexane-6-endo-carboxaldehyde neopentyl glycol acetal (Example 8, 0.48 g.) is treated at 0° C. with 25 ml. of 88% formic acid for 2.75 hr. The mixture is diluted with 500 ml. of brine, and extracted with 200 ml. of ethyl acetate. The organic phase is washed with brine and saturated aqueous sodium bicarbonate, and dried over sodium sulfate. Concentration under reduced pressure yields an oil, which when subjected to silica gel chromatography (eluting with 10–30% ethyl acetate-Skellysolve B) yields the title compound as an oil, 0.25 g. having NMR peaks at 1.22, 3.67, 5.15–5.57, 6.87–7.42, and 9.67 $\delta$ (doublet, J=4 H$_z$); and $R_f$0.26 (TLC on silica gel in ethyl acetate-Skellysolve B (25:75)).

EXAMPLE 10 dl-2-Exo-{m-[2-(methoxycarbonyl)ethyl]benzyl}-3-exo-(pivaloyloxy)-6-endo(cis-1-heptenyl)bicyclo[3.1.0]hexane (Formula LXVIII, wherein $R_3$ is hydrogen, $R_{16}$ is pivaloyl, $R_{20}$ is methyl, and ~ is endo).

Refer to Chart E step (e). The formula-LXVII aldehyde, i.e. dl-2-exo-{m-[2-(methoxycarbonyl)ethyl]benzyl}-2-exo(pivaloyloxy)bicyclo[3.1.0]hexane-6-endo-carboxaldehyde (Example 9, 0.25 g.) in 5 ml. of benzene is added to the Wittig ylid reagent (prepared in 15 ml. of benzene from n-hexyltriphenylphosphonium bromide (0.60 g.) and n-butyllithium (0.52 ml. of 2.32 M. solution of hexane) at about 25° C. for 0.5 hr. and using the supernatant). After 0.5 hr. there is added 1.0 ml. of acetone and the mixture stirred at 25° C. for 10 min. The mixture is diluted with 250 ml. of brine and extracted with 200 ml. of ethyl acetate. The organic phase is washed with brine and dried over magnesium sulfate. Concentration under reduced pressure yields an oil, 0.54 g., which when subjected to silica gel chromatography (eluting with dichloromethane) yields the title compound as an oil, 0.20 g. having $R_f$ 0.66 (TLC on silica gel in 25% ethyl acetate-Skellysolve B) and NMR peaks at 0.88, 1.19, 1.25, 3.68, 4.68–6.03 and 6.86–7.43 δ.

Thereafter, following the procedures of Chart F, the product of Example 10 is converted to the racemic glycol corresponding to formula LXXIV wherein $R_1$ is methyl and thence to dl-4,5,6-trinor-3,7-nter-m-phenylene-PGF$_{1\alpha}$, methyl ester, corresponding to formula LXXV, a useful compound.

EXAMPLE 11 dl-2-Exo-[m-(2-carboxyethyl)benzyl]-3-exo-hydroxy-6-endo-(cis-1-heptenyl)bicyclo[3.1.0]hexane (Formula LXIX wherein $R_1$ and $R_3$ are hydrogen, and ~ is endo); and dl-2-Exo-{m-[2-(methoxycarbonyl)ethyl]benzyl}-3-exo-hydroxy-6-endo-(cis-1-heptenyl)-bicyclo[3.1.0]hexane (Formula LXIX wherein $R_1$ is methyl, $R_3$ is hydrogen, and ~ is endo).

(I). Refer to Chart E, step (f). The formula-LXVIII diester, i.e. dl-2-exo-{m-[2-(methoxycarbonyl)ethyl]benzyl}-3-exo-(pivaloyloxy)-6-endo-(cis-1-heptenyl)-bicyclo[3.1.0]hexane (Example 10, 0.20 g.) is treated in 5 ml. of methanol with 2.0 ml. of 25% sodium methoxide in methanol at about 25° C. for 15 hr., then at reflux for 4 hr. The reaction mixture is acidified with 2 ml. of glacial acetic acid and then concentrated under reduced pressure. The residue is taken up in 200 ml. of ethyl acetate, washed with brine and dried over sodium sulfate. Concentration under reduced pressure yields the formula-LXIX title compound wherein $R_1$ is hydrogen as a pale yellow oil.

(II). The product of step (I) above in methanol, is converted to the methyl ester with diazomethane at 25° C. for 3–5 min. washed in ethyl acetate solution with saturated aqueous sodium bicarbonate and brine and dried over sodium sulfate to the formula-LXIX title compound wherein $R_1$ is methyl, an oil, 0.18 g. having $R_f$ 0.20 (TLC on silica gel in 25% ethyl acetate-Skellysolve B).

EXAMPLE 12 dl-2-Exo-{m-[2-(methoxycarbonyl)ethyl]benzyl}-6-endo-(cis-1-heptenyl)-bicyclo[3.1.0]hexane-3-one (Formula LXX: $R_1$ is methyl, $R_3$ is hydrogen, and ~ is endo).

Refer to Chart E, step (g). The formula-LXIX hydroxy compound, i.e. dl-2-exo-{m-[2-(methoxycarbonyl)ethyl]benzyl}-3-exo-hydroxy-6-endo-(cis-1-heptenyl)-bicyclo[3.1.0]hexane is oxidized as follows. The formula-LXIX compound wherein $R_1$ is methyl (Example 11, 0.18 g.) in dichloromethane is added to a solution of Collins reagent (prepared from pyridine (0.48 g. and chromium trioxide (0.3 g.) in 10 ml. dichloromethane at about 25° C. for 20 min.). The reaction mixture is then shaken with a mixture of 100 ml. of diethyl ether and 300 ml. of brine. The organic phase is shaken with a mixture of ice and 1 N. aqueous sodium hydroxide, then washed with water, saturated aqueous copper (II) sulfate, water, and brine, and dried over sodium sulfate. Concentration under reduced pressure yields a pale yellow oil, 0.20 g., which when subjected to silica gel chromatography (eluting with 5–10% ethyl acetate-Skellysolve B) yields the title compound, a colorless oil, 0.07 g., having $R_f$ 0.61 (TLC on silica gel in 25% ethyl acetate-Skellysolve B); NMR peaks at 0.88, 3.67, 4.68–5.18, 5.27–5.97, and 6.95–7.35 δ; infrared absorption bands at 2960, 2920, 2850, 1740, 1610, 1590, 1490, 1440, 1365, 1260, 1240, 1195, 1155, 1060, 785, and 705 cm$^{-1}$; and mass spectral peaks at 368, 350, 337, 326, 191, and 177.

Thereafter, following the procedures of Chart E, the product of Example 12 is converted to the racemic glycol corresponding to formula LXXI wherein $R_1$ is methyl and thence to dl-4,5,6-trinor-3,7-inter-m-phenylene-PGE$_1$, methyl ester, corresponding to formula LXXII, a useful compound.

Following the procedures of Examples 7–12 but using the optically active form of starting material XXX (from Example 6), there are obtained the corresponding optically active intermediates and final products.

Preparation 9

3-[3-(tert-Butyldimethylsilyloxy)propyl]-phenyllithium Cuprate Reactant

I. There is first prepared 1-bromo-3-[3-(tert-butyldimethylsiloxy)-propyl]benzene:

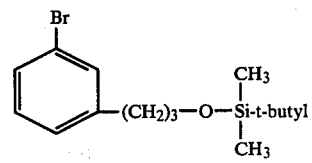

A solution of 3-(3-bromophenyl)-propan-1-ol (4.30 g.) in 15 ml. of dimethylformamide is treated with t-butyldimethylchlorosilane (3.62 g.) and imidazol (3.40 g.) at 25° C. for 3.5 hr. The mixture is diluted with brine and extracted with diethyl ether-Skellysolve B (1:1). The extracts are washed with 1 N. hydrochloric acid, aqueous sodium bicarbonate and brine, and dried over magnesium sulfate. Upon concentrating, 6 g. of oil is recovered, which, on distillation yields 5.68 g. of the silyl derivative, b. 84°–86° C./0.15 mm.

II. A solution of the above bromo compound (0.82 g.) in 20 ml. of diethyl ether is treated at −78° C. with tert-butyllithium (2.25 ml. of 1.20 M. solution in pentane), and stirred for 0.5 hr. The resulting solution of aryllithium compound is added to CuI. (n-C$_4$H$_9$)$_3$P complex prepared independently from copper (I) iodide (0.238 g.) in ti(n-butyl)phosphine (0.253 g.) in 20 ml. diethyl ether at 25° C. for 45 min. and cooled to −78° C. The resulting lithium cuprate reagent is then used directly in solution without isolation.

EXAMPLE 13

5α-(tert-Butyldimethylsiloxy)-3α-hydroxy-2β-[(3'S)-3'-hydroxy-trans-1'-octenyl]-1α-cyclopentanacetic Acid, 3,3'-Bistetrahydropyranyl Ether (Formula LXXXVI: Q$_4$ is

where THP is tetrahydropyran-2-yl, R$_{37}$ is THP, and Si(A)$_3$ is tert-butyldimethylsilyl).

I. Refer to Chart H, step (b). A solution of formula-LXXXIII lactone, specifically 3α,5α-dihydroxy-2β-[(3'S)-3'-hydroxy-trans-1'-octenyl]-1α-cyclopentan acetic acid, bistetrahydropyranyl ether (Corey et al., J. Am. Chem. Soc. 92, 397 (1970), 1.14 g.) in 10 ml. of methanol is treated with 10 ml. of 1 N. aqueous sodium hydroxide at about 25° C. for 2 hr. The reaction mixture is then concentrated to about one-half its volume, diluted with 50 ml. of water and saturated with sodium chloride. The pH is adjusted to about 5–6 with 1 M. aqueous potassium hydrogen sulfate and the mixture is extracted with ethyl acetate. The organic phase is washed with brine, dried over sodium sulfate, and concentrated to the formula-LXXXIV compound, an oil.

II. Step (c). The resulting triol acid, bistetrahydropyranyl ether is taken up in 5 ml. of dimethylformamide and added to a solution of tert-butyldimethylchlorosilane (0.94 g.) and imidazole (0.88 g.) in 15 ml. of dimethylformamide. The mixture is stirred at 25° C. and after about 17 hr. additional reagents are added (0.47 g. of tert-butyldimethylsilyl chloride and 0.44 g. of imidazole) and stirring continued first at 25° C. for one hr. and then at 40° C. for 3 hr., the reaction then being complete as shown by TLC. The reaction mixture is cooled, diluted with brine, and extracted with 400 ml. of Skellysolve B-diethyl ether (1:1). The organic phase is separated, washed with 1 N. hydrochloric acid and brine, dried over sodium sulfate, and concentrated to yield the formula-LXXXV compound.

III. Step (d). The residue from step (c) is dissolved in 175 ml. of a mixture of methanol-tetrahydrofuran-water (100:50:25) and treated with potassium carbonate (3.0 g.) at 25° C. for one hr. The reaction mixture is concentrated, diluted with 200 ml. of brine, adjusted to pH 4–5 with 1 M. aqueous potassium hydrogen sulfate, and extracted with ethyl acetate. The organic phase is washed with brine, dried over sodium sulfate, and concentrated to an oil containing the formula-LXXXVI title compound. The product is subjected to silica gel chromatography, eluting with ethyl acetate (10–20%)-Skellysolve B, to yield the formula-LXXXVI title compound, an oil, 1.36 g., having R$_f$ 0.14 (TLC on silica gel in ethyl acetate-Skellysolve B (1:3)), and NMR peaks at 0.3, 0.89, 0.7–2.8, 3.2–4.47, 4.68, 5.27–5.72, and 9.63 δ; and IR absorption bands at 2980, 2890, 1735, 1710, 1460, 1253, 1198, 1183, 1130, 1110, 1074, 1019, 981, 870, 838 and 776 cm$^{-1}$.

EXAMPLE 14

1-(tert-Butyldimethylsilyloxy)-2-methylene-4α-hydroxy-3β-[(3'S)-3'-hydroxy-trans-1'-octenyl]cyclopentane, 4,3'-Bistetrahydropyranyl Ether (Formula LXXXVII: Q$_4$, R$_{37}$, and Si(A)$_3$ as defined in Example 13).

Refer to Chart H, step (e). A mixture of the formula-LXXXVI silylated acid (Example 13, 2.20 g.) in 35 ml. of benzene is stirred with copper (II) acetate monohydrate (0.19 g.) and 1.16 ml. of pyridine until a homogeneous solution is produced. There is then added 5.03 g. of lead tetraacetate and the mixture stirred at about 25° C. in a dark place for 1.5 hr., with a slow stream of nitrogen passing through the mixture. With continued passage of nitrogen, the mixture is heated to 80° C. within 30 min. and kept at 80° C. for an additional 45 min. The course of the reaction is monitored with TLC. The reaction mixture is finally cooled to about 25° C., diluted with 300 ml. of brine, and extracted with ethyl acetate. The organic phase is washed with brine, dried over sodium sulfate, and concentrated to a residue containing the title compound, 2.25 g. The residue is subjected to silica gel chromatography, eluting with ethyl acetate (5–45%)-Skellysolve B, to yield the formula-LXXXVII title compound, 0.80 g., having R$_f$ 0.64 (TLC on silica gel in ethyl acetate-Skellysolve B (1:3)); NMR peaks at 0.08, 0.92, 0.75–2.9, 2.9–4. 4.72, 4.93, 5.17, and 5.33–5.64 δ; and IR absorption bands at 2960, 2895, 1460, 1345, 1251, 1199, 1120, 1075, 1065, 1034, 1020, 1002, 973, 900, 870, 838, 817, and 775 cm$^{-1}$.

EXAMPLE 15

2-Methylene-4α-hydroxy-3β-[(3'S)-3'-hydroxytrans-1'-octenyl]-cyclopentanol, 4,3'-Bistetrahydropyranyl Ether (Formula LXXXVIII: Q$_4$ and R$_{37}$ as defined in Example 13).

Refer to Chart H, step (f). A solution of the formula-LXXXVII silylated compound (Example 14, 3.40 g.) in 40 ml. of tetrahydrofuran is treated with 15 ml. of 0.6 M. tetra-n-butylammonium fluoride and the mixture is stirred at about 25° C. for one hr. The resulting mixture is diluted with 300 ml. of brine and extracted with diethyl ether. The organic phase is washed with brine, dried over magnesium sulfate, and concentrated. The residue (3.77 g.) is subjected to silica gel chromatography, eluting with ethyl acetate (10–50%)-Skellysolve B, to yield the formula-LXXXVIII title compound, now free of silyl groups, 1.94 g., a white solid, having R$_f$ 0.19 (TLC on silica gel in ethyl acetate-Skellysolve B (1:3)). An analytical sample, obtained on recrystallizing from Skellysolve B, has m.p. 83°–84.5° C.; NMR peaks at 0.88, 0.6–2.8, 3.0–4.5, 4.70, 5.02, and 5.20–5.62 δ; and IR absorption bands at 3220, 3140, 1660, 1125, 1080, 1065, 1040, 1020, 1000, 970, and 910 cm$^{-1}$.

EXAMPLE 16

2-Methylene-4α-hydroxy-3β-[(3'S)-3'-hydroxytrans-1'-octenyl cyclopentanone, 4,3'-Bistetrahydropyranyl Ether (Formula LXXXIX: Q$_4$ and R$_{37}$ as defined in Example 13).

Refer to Chart H, step (g). A solution of the formula-LXXXVIII allylic alcohol (Example 15, 0.41 g.) in 10 ml. of acetone is treated at −20° C. with 0.50 ml. of 2.67

M. Jones Reagent (Refer to Merck Index, Eighth Edition, page 1182 and references cited therein). The mixture is stirred at −20° to −15° C. for 30 min. and is then quenched with 0.25 ml. of isopropyl alcohol, stirring for an additional 10 min. The reaction mixture is then diluted with brine and extracted with diethyl ether. The organic phase is washed with aqueous sodium bicarbonate solution and brine, dried over sodium sulfate, and concentrated to the formula-LXXXIX title compound, 0.39 g., having IR absorption bands at 2980, 1735, 1647, 1200, 1129, 1112, 1076, 1035, 1020, and 978 cm$^{-1}$; and NMR peaks at 0.91, 0.8–3.1, 3.1–4.4, 4.68, 5.11, 5.47, 5.98 δ; and having $R_f$ 0.44 (TLC on silica gel in ethyl acetate-Skellysolve B (1:3)).

EXAMPLE 17

2α-[7-(tert-Butyldimethylsilyloxy)-2,3,4-trinor-1,5-inter-m-phenylene-heptyl]-4α-hydroxy-3β-[(3′S)-3′-hydroxy-trans-1-octenyl]cyclopentanone, 4,3′-Bistetrahydropyranyl Ether (Formula XC: $Q_4$, $R_{37}$, and Si(A)$_3$ as defined in Example 13).

Refer to Chart H, step (h). A solution of the formula-LXXXIX enone compound of Example 16 (0.39 g.) in 4 ml. of diethyl ether at −78° C. is added to a solution of lithium cuprate reagent (Preparation 9) at −78° C. during 5–10 min. and thereafter stirred at −78° C. for 30 min. The reaction mixture is added, with rapid stirring, to a mixture of 50 ml. of 1 M. potassium hydrogen sulfate, 50 ml. of brine, and ice, diluted with brine, and extracted with diethyl ether. The organic extracts are washed with aqueous sodium bicarbonate and brine, dried over sodium sulfate, and concentrated to an oil, 1.50 g. The oil is subjected to silica gel chromatography, eluting with ethyl acetate (10–30%)-Skellysolve B, to yield the title compound, an oil, 0.49 g., having infrared spectral absorption bands at 2980, 2890, 1749, 1251, 1200, 1128, 1108, 1077, 1037, 1020, 974, 837, 776 cm$^{-1}$; NMR peaks at 0.004, 0.9, 0.9–3.05, 3.1–4.3, 3.62, 4.63, 5.43, and 6.68–7.37 δ; $R_f$ 0.30 and 0.35 (TLC on silica gel plate in ethyl acetate-Skellysolve B (1:3)).

EXAMPLE 18

2α-[7-(tert-Butyldimethylsilyloxy)-2,3,4-trinor-1,5-inter-m-phenylene-heptyl]-4α-hydroxy-3β-[(3′S)-3′-hydroxy-trans-1-octenyl cyclopentanol, 4,3′-Bistetrahydropyranyl Ether (Formula XCI: $Q_4$, $R_{37}$, and Si(A)$_3$ as defined in Example 13).

Refer to Chart H, step (i). A solution of the formula-XC ketone of Example 17 (0.49 g.) in 10 ml. of methanol is treated at 0° C. with sodium borohydride (0.060 g.) in 2 ml. of water. Tetrahydrofuran (5 ml.) is added and the mixture is stirred at 0° C. for one hr. The mixture is concentrated, diluted with brine, and extracted with ethyl acetate. The organic phase is washed with brine, dried over sodium sulfate, and concentrated to give the formula-XCI title compound, an oil, 0.48 g., having $R_f$ 0.29 and 0.16 (TLC on silica gel plate is ethyl acetate-Skellysolve B (1:3)).

EXAMPLE 19

2α-(7-Hydroxy-2,3,4-trinor-1,5-inter-m-phenylene-heptyl)-4α-hydroxy-3β-[(3′S)-3′-hydroxytrans-1-octenyl]-cyclopentanol, 4,3′-Bistetrahydropyranyl Ether (Formula XCII: $Q_4$ and $R_{37}$ as defined in Example 13).

Refer to Chart H, step (j). A solution of the formula-XCI reduction product (Example 18, 0.48 g.) in 10 ml. of tetrahydrofuran is treated with tetra(n-butyl)ammonium fluoride (3 ml. of 0.5 M. solution at 25° C. for one hr., and then with an additional 1 ml. of tetra(n-butyl)ammonium fluoride solution for an additional hour. Brine is added and the mixture is extracted with ethyl acetate. The organic phase is washed with brine, dried over sodium sulfate, and concentrated to the formula-XCII title compound, an oil, 0.57 g., having $R_f$ 0.16 and 0.08 (TLC on silica gel plate in ethyl acetate-Skellysolve B (1:1)).

EXAMPLE 20

4,5,6-Trinor-3,7-inter-m-phenylene-PGE$_1$, 11,15-Bistetrahydropyranyl Ether. (Formula XCIII: $Q_4$ and $R_{37}$ as defined in Example 13).

Refer to Chart H, step (k). A solution of the formula-XCII compound of Example 19 (0.82 g.) in 30 ml. of acetone is treated at 20° C. with Jones reagent (2.0 ml. of 2.67 M. solution prepared from 2.1 g. chromium trioxide, 6 ml. of water and 1.7 ml. of concentrated sulfuric acid). After 1.6 hr. the reaction is complete and is quenched with 1.0 ml. of isopropyl alcohol, at 0° C. for 10 min. The mixture is diluted with brine and extracted with ethyl acetate. The organic phase is washed with brine, dried over sodium sulfate and concentrated to formula-XCIII title compound, an oil, 0.86 g., having $R_f$=0.59 (TLC on silica gel plate in A-IX system).

The "A-IX system" for TLC is described by Hamberg and Samuelsson, J. Biol. Chem. 241, 257 (1966), and is based on ethyl acetate-acetic acid-2,2,4-trimethylpentane-water (90:20:50:100).

EXAMPLE 21

4,5,6-Trinor-3,7-inter-m-phenylene-PGE$_1$

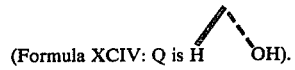

(Formula XCIV: Q is H   OH).

Refer to Chart H, step (I). A solution of the formula-XCIII compound of Example 20 (0.86 g.) in 15 ml. of acetic acid-water-tetrahydrofuran (20:10:3) is left at about 25° C. for 19 hr. The mixture is then diluted with 20 ml. of water and concentrated. The residue is taken up in 5 ml. of dichloromethane and subjected to silica gel chromatography, eluting with ethyl acetate (50–100%)-Skellysolve B, to yield the formula-XCIV title compound, 0.25 g., m. 67°–77° C., $R_f$ 0.19 (TLC on silica gel in A-IX system). An analytical sample, obtained by recrystallizing from diethyl ether-Skellysolve B, has m.p. 65.9°–69.5° C.; NMR peaks at 0.95, 1.2–1.7, 1.9–3.2, 3.9–4.2, 5.3–5.7, 5.9–6.2, and 6.9–7.3 δ; [α]$_D$ −87° (c=0.8465 in chloroform); and mass spectral peaks (TMS derivative) at 604.3408, 589, 533, 514, 499, 443, 417, 389, 313, 279, and 199.

Following the procedures of Examples 13–21, but replacing the formula-LXXXIII lactone starting material with the appropriate lactone wherein the terminal pentyl group of the octenyl side chain of 3α,5α-dihydroxy-2β-[(3′S)-3′-hydroxy-trans-1′-octenyl]-1α-cyclopentanacetic acid, bistetrahydropyranyl ether is replaced by each of the following groups, as known in the art or available by methods known in the art:
1-methylpentyl
1,1-dimethylphenyl
1-fluoropentyl
1,1-difluoropentyl
phenoxymethyl
(m-tolyloxy)methyl (p-tolyloxy)methyl
(m-chlorophenoxy)methyl
(p-chlorophenoxy)methyl
(m-fluorophenoxy)methyl
(p-fluorophenoxy)methyl
(m-trichloromethylphenoxy)methyl
(p-trichloromethylphenoxy)methyl
(m-anisyloxy)methyl
(p-anisyloxy)methyl
1-phenoxyethyl
1-methyl-1-phenoxyethyl
benzyl
2-phenethyl
2-(m-tolyl)ethyl
2-(p-tolyl)ethyl
2-(m-chlorophenyl)ethyl
2-(p-chlorophenyl)ethyl
2-(m-fluorophenyl)ethyl
2-(p-fluorophenyl)ethyl
2-(m-trichloromethylphenyl)ethyl
2-(p-trichloromethylphenyl)ethyl
2-(m-anisyl)ethyl
2-(p-anisyl)ethyl
3-phenylpropyl
1-methyl-1-phenylethyl
1-methyl-2-phenylethyl
1,1-dimethyl-2-phenylethyl
1,1-dimethyl-3-phenylpropyl
α,α-difluorobenzyl
1-fluoro-2-phenylethyl
1,1-difluoro-2-phenylethyl and
1,1-difluoro-3-phenylpropyl
there are obtained each of the corresponding formula-XCIV 4,5,6-trinor-3,7-inter-m-phenylene-PGE$_1$ analogs having one of the following structural features:
16-methyl-;
16,16-dimethyl-;
16-fluoro-;
16,16-difluoro-;
16-phenoxy-17,18,19,20-tetranor-;
16-(m-tolyloxy)-17,18,19,20-tetranor-;
16-(p-tolyloxy)-17,18,19,20-tetranor-;
16-(m-chlorophenoxy)-17,18,19,20-tetranor-;
16-(p-chlorophenoxy)-17,18,19,20-tetranor-;
16-(m-fluorophenoxy)-17,18,19,20-tetranor-;
16-(p-fluorophenoxy)-17,18,19,20-tetranor-;
16-(m-trichloromethylphenoxy)-17,18,19,20-tetranor-;
16-(p-trichloromethylphenoxy)-17,18,19,20-tetranor-;
16-(m-anisyloxy-17,18,19,20-tetranor-;
16-(p-anisyloxy)-17,18,19,20-tetranor-;
16-phenoxy-18,19,20-trinor-;
16-methyl-16-phenoxy-18,19,20-trinor;
16-phenyl-17,18,19,20-tetranor-;
17-phenyl-18,19,20-trinor-;
17-(m-tolyl)-18,19,20-trinor-;
17-(p-tolyl)-18,19,20-trinor-;
17-(m-chlorophenyl)-18,19,20-trinor-;
17-(p-chlorophenyl)-18,19,20-trinor-;
17-(m-fluorophenyl)-18,19,20-trinor-;
17-(p-fluorophenyl)-18,19,20-trinor-;
17-(m-trichloromethylphenyl)-18,19,20-trinor-;
17-(p-trichloromethylphenyl)-18,19,20-trinor-;
17-(m-anisyl)-18,19,20-trinor-;
17-(p-anisyl)-18,19,20-trinor-;
18-phenyl-19,20-dinor-;
16-methyl-16-phenyl-18,19,20-trinor-;
16-methyl-17-phenyl-18,19,20-trinor-;
16,16-dimethyl-17-phenyl-18,19,20-trinor-;
16,16-dimethyl-18-phenyl-19,20-dinor-;
16,16-difluoro-16-phenyl-17,18,19,20-tetranor-;
16-fluoro-17-phenyl-18,19,20-trinor-;
16,16-difluoro-17-phenyl-18,19,20-trinor-; or
16,16-difluoro-18-phenyl-19,20-dinor-.

For example, starting with 3α,5α-dihydroxy-2β-[(3'S)-3'-hydroxy-trans-1'-(5'-phenyl)pentenyl]-1α-cyclopentanacetic acid, bis tetrahydropyranyl ether there is obtained 4,5,6,18,19,20-hexanor-3,7-inter-m-phenylene-17-phenyl-PGE$_1$.

Likewise starting with the corresponding (3'R)-3'-hydroxy lactones, there are obtained the 15-epimeric products.

EXAMPLE 22

4,5,6-Trinor-3,7-inter-m-phenylene-PGE$_1$, Methyl Ester

(Formula-XCVI: Q is H    OH).

Refer to Chart I.

I. A solution of the formula-XCIII compound of Example 20 (0.56 g.) in 10 ml. of methanol and 5 ml. of diethyl ether is treated with diazomethane at 0° C. for about 5 min. The reaction mixture is quenched with aqueous 10% acetic acid, diluted with brine and extracted with ethyl acetate. The organic phase is washed with aqueous sodium bicarbonate and brine, dried over sodium sulfate, and concentrated to the formula-XCV compound, an oil, 0.44 g., having R$_f$0.52 (TLC on silica gel plate in ethyl acetate-Skellysolve B (1:1)).

II. A solution of the above formula-XCV compound (0.44 g.) in 10 ml. of acetic acid-water-tetrahydrofuran (6:3:1) is stirred at about 38°–40° C. for 4.5 hr. The mixture is diluted with brine and sodium bicarbonate and extracted with ethyl acetate. The organic phase is washed with aqueous sodium bicarbonate and brine, dried over sodium sulfate and concentrated to an oil, 0.30 g. The residue is subjected to silica gel chromatography, eluting with acetone (10–30%)-dichloromethane to give the formula-XCVI product, 0.16 g. m. 54.9°–57.9° C.; having R$_f$ 0.21 (TLC on silica gel in acetone-dichloromethane (3:7)); infrared spectral bands at 3320, 1745, 1725, 1610, 1590, 1490, 1245, 1210, 1165, 1145, 1085, 1020, and 970 cm$^{-1}$; NMR peaks at 0.91, 1.35, 3.65, 5.45, and 6.69–7.36 δ; and mass spectral peaks (TMS derivative) at 546.3204, 531, 515, 475, 456, 385, 359, 331, 279, 225, 199, and 177.

EXAMPLE 23

4,5,6-Trinor-3,7-inter-m-phenylene-PGE$_1$ (formula V).

The free acid is obtained from the methyl ester by use of an esterase enzyme as disclosed in U.S. Pat. No. 3,761,356.

A solution of 4,5,6-trinor-3,7-inter-m-phenylene-PGE$_1$, methyl ester (Example 22, 0.04 g.) in 1.5 ml. of 95% ethanol and 8.2 ml. of water is treated with an esterase enzyme composition obtained from Plexaura homoalla according to the above-cited patent (0.4 g.) at about 25° C. for 24 hr. The mixture is diluted with 40 ml. of acetone, adjusted to pH 3 with potassium hydrogen sulfate, and filtered. The filtrate is diluted with brine and extracted with ethyl acetate. The organic phase is washed with brine, dried over sodium sulfate and concentrated to yield an oil, 0.03 g., containing the title compound, R$_f$ 0.19 (TLC on silica gel in A-IX system).

EXAMPLE 24

2-Methylene-4α-hydroxy-3β-[(3'S)-3'-hydroxy-trans-1'-octenyl]-cyclopentanol, 4,3'-Bis-tetrahydropyranyl Ether (Formula LXXXVIII: Q$_4$ and R$_{37}$ as defined in Example 13).

a. Refer to Chart J, step (a). A solution of formula-LXXXIII lactone (Corey et al., J. Am. Chem. Soc. 92, 397 (1970), 4.29 (g.) in 15 ml. of tetrahydrofuran is added dropwise to a stirred mixture of sodium bis(2-methoxyethoxy)aluminum hydride (70% solution in benzene, 4.3 g.) and 50 ml. of tetrahydrofuran at about 20° C. The mixture is stirred for an additional 2 hr. whereupon 100 ml. of 5% aqueous potassium hydroxide is added cautiously with stirring. The mixture is diluted with 200 ml. of diethyl ether and water (1:1). The organic phase is washed with 5% aqueous potassium hydroxide and brine, dried over sodium sulfate, and concentrated to yield the formula-XCVII compound, an oil, 4.59 g., having infrared absorption bands at 3450, 2980, 2890, 1465, 1450, 1438, 1346, 1338, 1200, 1130, 1110, 1075, 1034, 1020, 974, and 869 cm$^{-1}$.

b. Chart J, step (b). The diacylated formula-XCVIII compound is next obtained from the diol product XCVII of step (a) (4.59 g.) treated in 40 ml. of pyridine, and 10 ml. of acetic anhydride together with 0.1 g. of 4-dimethyl-aminopyridine as a catalyst. The reaction mixture is stirred at about 25° C. for 16 hours, then diluted with brine and extracted with diethyl ether. The organic phase is washed with ice-cold 1 M. potassium acid sulfate and brine, dried over sodium sulfate, and concentrated to yield the formula-XCVIII diacetate, an oil, 5.24 g.

c. Chart J, step (c). The product of step (b) (5.24 g.) is treated with potassium carbonate (0.14 g.) in 100 ml. methanol at about 40° C. for 1.25 hr. and finally at about 25° C. for 0.75 hr. The mixture is diluted with ice cold brine and 1 M. potassium acid sulfate to pH 2-3 and extracted with ethyl acetate. The organic phase is washed with brine, dried over sodium sulfate, and concentrated to an oil containing the formula-XCIX monoacetate, 4.56 g. The residue is subjected to silica gel chromatography, eluting with acetone (5–75%)-dichloromethane to obtain the formula-XCIX compound, an oil, 0.69 g., having R$_f$ 0.20 (TLC on silica gel in acetonedichloromethane (15:85)); infrared absorption bands at 3530, 2970, 1740, 1242, 1130, 1111, 1073, 1032, 1020, 972 cm$^{-1}$; NMR peaks at 0.88, 0.7–3.0, 2.03, 3.15–4.3, 4.65, 5.13, 5.3–5.82δ.

d. Chart J. step (d). The product of step (c) (0.69 g.) in 20 ml. of acetone is treated with 1.5 ml. of 2.67 M. Jones reagent added dropwise. The mixture is stirred at about 25° C. for 0.5 hr., diluted with brine, and extracted with diethyl ether. The ether extract is washed with brine, dried over sodium sulfate, and concentrated to an oil, 0.58 g. The residue is subjected to silica gel chromatography, eluting with ethyl acetate (10–50%)-Skellysolve B, to obtain the formula-C acid compound, 0.31 g., having R$_f$ 0.56 and 0.51 (TLC on silica gel in A-IX system); infrared absorption bands at 2970, 1745, 1240, 1032, and 1020 cm$^{-1}$; and NMR peaks at 0.89, 0.7–3.1, 2.05, 3.15–4.4, 4.65, 5.19, 5.46, 9.06δ.

e. Chart J, step (e). The product of step (d) (0.31 g.) is treated in 10 ml. of benzene with 0.12 ml. of pyridine and 0.02 g. of copper (II) acetate monohydrate. After stirring in a dark place at about 25° C. for 45 min., the mixture is treated with 0.52 g. of lead tetraacetate. The mixture is stirred, first at about 25° C. for 45 min., then heated up to 80° C. in 15 min. and at 80° C. for 10 min. The mixture is cooled, diluted with brine, and extracted with ethyl acetate. The organic phase is washed with brine, dried over sodium sulfate, and concentrated to an oil, 0.37 g. The residue is subjected to silica gel chromatography, eluting with ethyl acetate (20–50%)-Skellysolve B, to yield the formula-CI methylene compound, 0.03 g., having R$_f$ 0.61 (TLC on silica gel in ethyl acetate-Skellysolve B(1:1); infrared absorption bands at 2970, 1740, 1235, 1035, and 1020 cm$^{-1}$; and NMR peaks at 0.90, 0.8–3.0, 2.07, 3.1–4.3, 4.67, 5.00, 5.27, and 5.43δ.

f. Chart J, step (f). Finally, the formula-LXXXVIII title compound is obtained by saponification of the remaining acyl group on the product of step (e) (0.03 g.) treated in 2 ml. of methanol with 0.02 g. of potassium carbonate at about 25° C. for 45 min. The reaction mixture is diluted with brine and extracted with ethyl acetate. The extract is washed with brine, dried over sodium sulfate, and concentrated to yield the title compound, an oil, 0.22 g., having R$_f$ identical with that for the formula-LXXXVIII product of Example 15 above.

EXAMPLE 25

2-Methylene-4α-hydroxy-3β-[(3'S)-3'-hydroxy-trans-1'-octenyl]-cyclopentanol, 4,3'-Bis-tetrahydropyranyl Ether (Formula LXXXVIII: Q$_4$ and R$_{37}$ as defined in Example 13).

a. Refer to Chart J, step (b). The compound of formula-XCVIII wherein R$_{17}$ in the terminal position of the chain is acetyl and R$_{17}$ on the ring is pivaloyl is prepared in two stages. The monoacetate is first prepared from compound XCVII (Example 24a, 5.56 g.), 50 ml. of pyridine, and 1.45 ml. of acetic anhydride, stirred at 0° C. for 2 hr., then allowed to warm to about 20° C. in 16 hr. The mixture is diluted with brine and extracted with ethyl acetate. The organic phase is washed with 1 N. hydrochloric acid to pH 2 in the washings, then with brine, dried, and concentrated to an oil, 5.88 g. The residue is subjected to silica gel chromatography, eluting with ethyl acetate (10–100%)-Skellysolve B, to yield the monoacetate, 3.41 g., having R$_f$ 0.29 (TLC on silica gel in ethyl acetate-Skellysolve B (1:1); infrared absorption bands at 3530, 2975, 2890, 1745, 1239, 1133, 1077, 1032, 1020 and 981 cm$^{-1}$; and NMR peaks at 0.89, 0.9–2.8, 2.04, 3.1–4.38, 4.15, 4.72 and 5.53.

b. Continuing with Chart J, step (b). The product of step (a) above, having a terminal acetyl group on the chain (3.41 g.) is treated with 30 ml. of pyridine and 1.74 ml. of pivaloyl chloride at about 25° C. for 12 hr. The reaction is continued with additional 1.74 ml. of pivaloyl chloride at 40° C. for 3 hr. and at 23° C. for 16 hr. The reaction is quenched with 4 ml. of 85% lactic acid at 23° C. for one hr. The mixture is diluted with brine and extracted with ethyl acetate. The extract is washed with 1 N. hydrochloric acid-ice, sodium bicarbonate, and brine, dried over sodium sulfate, and concentrated to the formula-XCVIII compound having acetyl on the terminal position of the chain and pivaloyl on the ring. There is obtained 3.84 g., having R$_f$ 0.59 (TLC on silica gel in ethyl acetate-Skellysolve B (1:1)); infrared absorption bands at 2980, 2890, 1745, 1755, 1280, 1160, 1032, and 1020 cm$^{-1}$; and NMR peaks at 0.87, 1.19, 1.98, 4.03, 4.67, 5.10, and 5.52δ.

c. Chart J, step (c). The product of step (b) above (3.84 g.) is treated in 100 ml. of anhydrous methanol with 0.09 g. of potassium carbonate at about 25° C. for 0.5 hr. and at 40° C. for 1.5 hr. The reaction is continued with additional 0.09 g. of potassium carbonate at 40° C. for 2 hr. and at 24° C. for 16 hr. The mixture is concentrated and then diluted with brine and extracted with ethyl acetate. The organic phase is washed with brine, dried over sodium sulfate, and concentrated to yield the formula-XCIX product wherein $R_{17}$ is pivaloyl and $R_{37}$ is THP. There is obtained 3.42 g., having $R_f$ 0.34 (TLC on silica gel in ethyl acetate-Skellysolve B (1:1)).

d. Chart J. step (d). The product of step (c) above (3.42 g.) is oxidized to the formula-C acid in 75 ml. of acetone at 0° C. with 6.54 ml. of 2.67 M. Jones reagent. In one hour the reaction is quenched with 2 ml. of isopropyl alcohol, stirring at 0° C. for 15 min. The mixture is concentrated, diluted with brine, and extracted with ethyl acetate. The extract is washed with water and brine, dried over sodium sulfate, and concentrated to an oil, 3.44 g. The residue is subjected to silica gel chromatography, eluting with ethyl acetate (20–40%)-Skellysolve B to yield the formula-C acid, an oil, 1.99 g., having $R_f$ 0.69 and 0.74 (TLC on silica gel in A-IX system); and NMR peaks at 0.88, 1.18, 0.8–3.0, 3.1–4.3, 4.67, 5.16, 5.48, and 10.54δ.

e. Chart J, step (e). The product of step (d) above is subjected to oxidative decarboxylation to form the formula-CI compound. The formula-C acid (1.99 g.) is treated in 35 ml. of benzene with 0.18 g. of copper (I) acetate monohydrate and 1.11 ml. of pyridine at about 25° C. for one hr. Lead tetraacetate (4.80 g.) is added and stirring continued in a dark place at about 25° C. for one hour, then to 80° C. in 10 min. and at 80° C. for 25 min. The mixture is cooled, diluted with brine, and extracted with ethyl acetate. The extract is washed with brine, dried over sodium sulfate, and concentrated to an oil, 2.11 g. The residue is subjected to silica gel chromatography, eluting with ethyl acetate (5–40%)-Skellysolve B, to yield the formula-CI methylene compound wherein $R_{17}$ is pivaloyl and $R_{37}$ is THP. There is obtained an oil, 0.15 g., having $R_f$ 0.43 (TLC on silica gel in ethyl acetate-Skellysolve B (1:3)) and NMR peaks at 0.88, 0.8–2.9, 1.18, 3.0–4.4, 4.72, 5.00, 5.22, 5.45δ.

f. Chart J, step (f). Finally, the formula-LXXXVIII title compound is obtained by saponification of the product of step (e) above, using excess sodium hydroxide in aqueous methanol at about 25° C. until shown by TLC to be converted. Thereafter the usual work-up with brine, extracting, washing, and concentrating yields the title compound having the same properties as the product of Example 15 above.

EXAMPLE 26

2-Decarboxy-2-hydroxymethyl-4,5,6-trinor-3,7-inter-m-phenylene-PGF$_{1\alpha}$, 9-Acetate (Formula CIII: $Q_4$ is

where THP is tetrahydropyranyl, $R_{17}$ is acetyl, $R_{37}$ is THP, and $R_{38}$ is n-pentyl).

Refer to Chart K, steps (a) and (b). A solution of compound XCI (Example 18, 1.26 g.) in 15 ml. of pyridine is treated with 5 ml. of acetic anhydride and warmed to 45°–50° C. for 20 hr. The reaction mixture is diluted with brine and extracted with ethyl acetate. The combined extracts are washed with water, 1 N hydrochloric acid, saturated aqueous sodium bicarbonate, and brine, dried over sodium sulfate and concentrated to yield the formula-CII compound, an oil, having $R_f$ 0.37 (TLC on silica gel in 25% ethyl acetate in Skellysolve B).

A solution of the above formula-CII compound in 18 ml. of tetrahydrofuran is treated with 7 ml. of 0.5 M tetra-n-butylammonium fluoride in tetrahydrofuran. The reaction mixture is stirred at about 25° C. for 2.25 hr., diluted with brine and extracted with ethyl acetate. The combined extracts are washed with brine, dried over sodium sulfate, and concentrated. The residue is subjected to silica gel chromatography, eluting with ethyl acetate (30–60%)-Skellysolve B, to yield the title compound of formula CIII, 0.823 g., having $R_f$ 0.42 (TLC on silica gel in A-IX system.

EXAMPLE 27

4,5,6-Trinor-3,7-inter-m-phenylene-PGF$_{1\alpha}$ (Formula VII: Q is

$R_1$ is hydrogen, and $R_{38}$ is n-pentyl).

Refer to Chart K, steps (c), (d), and (e). A solution of alcohol CIII (Example 26, 0.84 g.) in 30 ml. of acetone is treated at −20° C. with 1 ml. of 2.67 M Jones Reagent. After one hr. the reaction is quenched with 0.5 ml. of isopropanol. The reaction mixture is diluted with brine and extracted with ethyl acetate. The combined extracts are washed with brine, dried over sodium sulfate, and concentrated to yield the formula-CIV acid, 0.89 g., having $R_f$ 0.58 (TLC on silica gel in A-IX system).

A solution of above acid CIV (0.89 g.) in 15 ml. of methanol is treated with 5 ml. of 5% aqueous potassium hydroxide and heated at reflux for 40 min. The reaction mixture is cooled to about 25° C., diluted with brine, acidified to pH 2–3 with ice-cold 1 M aqueous potassium hydrogen sulfate, and extracted with ethyl acetate. The combined extracts are washed with brine, dried over sodium sulfate, and concentrated to yield the formula-CV compound, 0.78 g., an oil having $R_f$ 0.42 (TLC on silica gel in A-IX system).

A solution of the above formula-CV compound (0.78 g.) in 15 ml. of acetic acid/water/tetrahydrofuran (20/10/3 by volume) is stirred at about 25° C. for 18 hr. The reaction mixture is then freeze-dried. The residue is subjected to silica gel chromatography, eluting with ethyl acetate (50–100%)-Skellysolve B followed by methanol (5%) in ethyl acetate, to give the formula CVI (VII) title compound, 0.27 g., a solid having $R_f$ 0.12 (TLC on silica gel in A-IX system). An analytical sample, obtained by recrystallizing from ethyl acetate-Skellysolve B, has m.p. 109.8°–112.0° C.; NMR peaks at 0.88, 3.67–4.23, 5.02, 5.43–5.67, and 6.8–7.3δ and mass spectral peaks at 372, 354, 300, 191, 163, 121, 117, 93, 91, 79, 67, 43, and 41.

Following the procedures of Examples 26 and 27 but replacing starting material XCI, i.e. 2α-[7-(tert-Butyldimethylsilyloxy)-2,3,4-trinor-1,5-inter-m-phenyleneheptyl]-4α-hydroxy-3β-[(3'S)-3'-hydroxy-trans-1-octenyl]cyclopentanol, 4,3'-bistetrahydropyranyl ether with each of the formula-XCI intermediates obtained from the formula-LXXXIII lactones listed following Example 21, there are obtained the corresponding formula-VII 4,5,6-trinor-3,7-inter-m-phenylene-PGF$_{1\alpha}$ analog having the structural features listed for the PGE$_1$ analogs obtained following Example 21.

EXAMPLE 28

4,5,6-Trinor-3,7-inter-m-phenylene-PGA$_1$ (Formula-VIII: Q is

and R$_{38}$ is n-pentyl).

A solution of 4,5,6-trinor-3,7-inter-m-phenylene-PGE$_1$ (Example 21, 0.070 g.) and one ml. of 0.5 N. hydrochloric acid in 2 ml. of tetrahydrofuran is left at about 25° C. for 5 days. The reaction mixture is then diluted with brine and extracted with ethyl acetate. The combined extracts are washed with brine, dried over sodium sulfate, and concentrated. The residue (0.070 g.) is dissolved in 2 ml. of methylene chloride and subjected to silica gel chromatography, eluting with ethyl acetate (30–100%)-Skellysolve B, to yield the formula-VIII title compound, 0.032 g., having R$_f$ 0.40 (TLC on silica gel in A-IX system); NMR peaks at 0.88, 0.9–1.7, 2.0–3.4, 3.92, 5.11–5.42, 6.00–6.35, 6.33, and 6.83–7.76$\delta$; and mass spectral peaks (TMS derivative) at 514.2943, 499, 443, 424, 415, 409, 353, 235, and 199.

Following the procedure of Example 28, but replacing that PGE$_1$ compound, namely 4,5,6-trinor-3,7-inter-m-phenylene-PGE$_1$, with each of the PGE$_1$-type analogs obtained and listed after Example 21, there are obtained the corresponding formula-VIII PGA$_1$-type compounds having the structural features listed for the PGE$_1$ analogs obtained following Example 21.

I claim:

1. An optically active compound of the formula

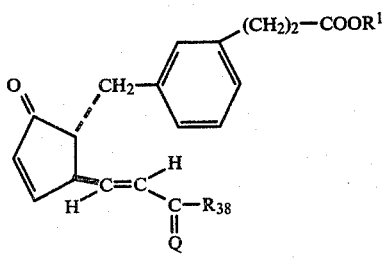

or a mixture comprising that compound and the enantiomer thereof, wherein Q is

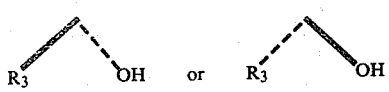

wherein R$_3$ is hydrogen or alkyl of one to 4 carbon atoms, inclusive;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the pharmacologically acceptable salts thereof when R$_1$ is hydrogen; wherein R$_{38}$ is

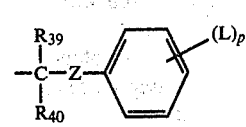

wherein R$_{39}$ and R$_{40}$ are hydrogen, alkyl of one to 4 carbon atoms, inclusive, or fluoro, being the same or different, with the proviso that one of R$_{39}$ and R$_{40}$ is fluoro only when the other is hydrogen or fluoro and the further proviso that neither R$_{39}$ nor R$_{40}$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_{39}$R$_{40}$— and the phenyl ring; and wherein L is alkyl of one to 4 carbon atoms, inclusive, fluoro, chloro, trifluoromethyl, or —OR$_{41}$— wherein R$_{41}$ is alkyl of one to 4 carbon atoms, inclusive, and p is zero, one, 2 or 3, with the proviso that not more than two L's are other than alkyl and when p is 2 or 3 the L's are either the same or different.

2. A compound according to claim 1 wherein Z is oxa (—O—).

3. A compound according to claim 2 wherein Q is

4. A compound according to claim 2 wherein Q is

5. A compound according to claim 4 wherein R$_{39}$ and R$_{40}$ are hydrogen, methyl, or ethyl, being the same or different.

6. A compound according to claim 5 wherein both R$_{39}$ and R$_{40}$ are hydrogen.

7. A compound according to claim 6 wherein R$_3$ is hydrogen.

8. A compound according to claim 7 wherein R$_1$ is alkyl of one to 12 carbon atoms.

9. A compound according to claim 7 wherein R$_1$ is hydrogen or a pharmacologically acceptable cation.

10. 4,5,6,17,18,19,20-Heptanor-3,7-inter-m-phenylene-16-phenoxy-PGA$_1$, a compound according to claim 9.

11. 4,5,6,17,18,19,20-Heptanor-3,7-inter-m-phenylene-16-(m-tolyloxy)-PGA$_1$, a compound according to claim 9.

12. 4,5,6,17,18,19,20-Heptanor-3,7-inter-m-phenylene-16-(p-tolyloxy)-PGA$_1$, a compound according to claim 9.

13. 4,5,6,17,18,19,20-Heptanor-3,7-inter-m-phenylene-16-(m-chlorophenoxy)-PGA$_1$, a compound according to claim 9.

14. 4,5,6,17,18,19,20-Heptanor-3,7-inter-m-phenylene-16-(p-chlorophenoxy)-PGA$_1$, a compound according to claim 9.

15. 4,5,6,17,18,19,20-Heptanor-3,7-inter-m-phenylene-16-(m-fluorophenoxy)-PGA$_1$, a compound according to claim 9.

16. 4,5,6,17,18,19,20-Heptanor-3,7-inter-m-phenylene-16-(p-fluorophenoxy)-PGA$_1$, a compound according to claim 9.

17. 4,5,6,17,18,19,20-Heptanor-3,7-inter-m-phenylene-16-(m-trifluoromethylphenoxy)-PGA$_1$, a compound according to claim 9.

18. 4,5,6,17,18,19,20-Heptanor-3,7-inter-m-phenylene-16-(p-trifluoromethylphenoxy)-PGA$_1$, a compound according to claim 9.

19. 4,5,6,17,18,19,20-Heptanor-3,7-inter-m-phenylene-16-(m-anisyloxy)-PGA$_1$, a compound according to claim 9.

20. 4,5,6,17,18,19,20-Heptanor-3,7-inter-m-phenylene-16-(p-anisyloxy)-PGA$_1$, a compound according to claim 9.

21. A compound according to claim 6 wherein $R_3$ is methyl.

22. A compound according to claim 5 wherein one or both of $R_{39}$ and $R_{40}$ are methyl.

23. A compound according to claim 22 wherein $R_3$ is hydrogen.

24. A compound according to claim 23 wherein $R_1$ is alkyl of one to 12 carbon atoms.

25. A compound according to claim 23 wherein $R_1$ is hydrogen or a pharmacologically acceptable cation.

26. 4,5,6,18,19,20-Hexanor-3,7-inter-m-phenylene-16-methyl-16-phenoxy-PGA$_1$, a compound according to claim 25.

27. A compound according to claim 1 wherein Z is $C_jH_{2j}$ wherein $C_jH_{2j}$ is as defined in claim 1.

28. A compound according to claim 27 wherein Q is

29. A compound according to claim 27 wherein Q is

30. A compound according to claim 29 wherein $R_{39}$ and $R_{40}$ are hydrogen, methyl, ethyl, or fluoro, being the same or different.

31. A compound according to claim 30 wherein $R_{39}$ and $R_{40}$ are both hydrogen.

32. A compound according to claim 31 wherein $R_3$ is hydrogen.

33. A compound according to claim 32 wherein $C_jH_{2j}$ is a valence bond.

34. 4,5,6,17,18,19,20-Heptanor-3,7-inter-m-phenylene-16-phenyl-PGA$_1$, a compound according to claim 33.

35. A compound according to claim 32 wherein $C_jH_{2j}$ is methylene.

36. 4,5,6,18,19,20-Hexanor-3,7-inter-m-phenylene-17-phenyl-PGA$_1$, a compound according to claim 35.

37. 4,5,6,18,19,20-Hexanor-3,7-inter-m-phenylene-17-(m-tolyl)-PGA$_1$, a compound according to claim 35.

38. 4,5,6,18,19,20-Hexanor-3,7-inter-m-phenylene-17-(p-tolyl)-PGA$_1$, a compound according to claim 35.

39. 4,5,6,18,19,20-Hexanor-3,7-inter-m-phenylene-17-(m-chlorophenyl)-PGA$_1$, a compound according to claim 35.

40. 4,5,6,18,19,20-Hexanor-3,7-inter-m-phenylene-17-(p-chlorophenyl)-PGA$_1$, a compound according to claim 35.

41. 4,5,6,18,19,20-Hexanor-3,7-inter-m-phenylene-17-(m-fluorophenyl)-PGA$_1$, a compound according to claim 35.

42. 4,5,6,18,19,20-Hexanor-3,7-inter-m-phenylene-17-(p-fluorophenyl)-PGA$_1$, a compound according to claim 35.

43. 4,5,6,18,19,20-Hexanor-3,7-inter-m-phenylene-17-(m-trifluoromethylphenyl)-PGA$_1$, a compound according to claim 35.

44. 4,5,6,18,19,20-Hexanor-3,7-inter-m-phenylene-17-(p-trifluoromethylphenyl)-PGA$_1$, a compound according to claim 35.

45. 4,5,6,18,19,20-Hexanor-3,7-inter-m-phenylene-17-(m-anisyl)-PGA$_1$, a compound according to claim 35.

46. 4,5,6,18,19,20-Hexanor-3,7-inter-m-phenylene-17-(p-anisyl)-PGA$_1$, a compound according to claim 35.

47. A compound according to claim 32 wherein $C_jH_{2j}$ is ethylene.

48. A compound according to claim 31 wherein $R_3$ is methyl.

49. A compound according to claim 30 wherein one or both of $R_{39}$ and $R_{40}$ are methyl.

50. A compound according to claim 49 wherein $R_3$ is hydrogen.

51. A compound according to claim 50 wherein $C_jH_{2j}$ is a valence bond.

52. A compound according to claim 50 wherein $C_jH_{2j}$ is methylene.

53. 4,5,6,18,19,20-Hexanor-3,7-inter-m-phenylene-16-methyl-17-phenyl-PGA$_1$, a compound according to claim 52.

54. 4,5,6,18,19,20-Hexanor-3,7-inter-m-phenylene-16,16-dimethyl-17-phenyl-PGA$_1$, a compound according to claim 52.

55. A compound according to claim 50 wherein $C_jH_{2j}$ is ethylene.

56. A compound according to claim 30 wherein one or both of $R_{39}$ and $R_{40}$ are fluoro.

57. A compound according to claim 56 wherein $R_3$ is hydrogen.

58. A compound according to claim 57 wherein $C_jH_{2j}$ is a valence bond.

59. A compound according to claim 57 wherein $C_jH_{2j}$ is methylene.

60. 4,5,6,18,19,20-Hexanor-3,7-inter-m-phenylene-16-fluoro-17-phenyl-PGA$_1$, a compound according to claim 59.

61. 4,5,6,18,19,20-Hexanor-3,7-inter-m-phenylene-16,16-difluoro-17-phenyl-PGA$_1$, a compound according to claim 59.

62. 4,5,6,19,20-Pentanor-3,7-inter-m-phenylene-18-phenyl-PGA$_1$, a compound according to claim 57.

* * * * *